US009999420B2

(12) United States Patent
Knapp et al.

(10) Patent No.: US 9,999,420 B2
(45) Date of Patent: *Jun. 19, 2018

(54) SHAPE MEMORY FILAMENT FOR SUTURE MANAGEMENT

(71) Applicants:DePuy Mitek, LLC, Raynham, MA (US); Thomas P. Knapp, Pacific Palisades, CA (US)

(72) Inventors: Thomas P. Knapp, Pacific Palisades, CA (US); Bernhard Uihlein, Dettingen (DE); Stanley O. Thompson, New Boston, NH (US); Timothy J. Coonahan, Sterling, MA (US); Jon Taylor, Groton, MA (US)

(73) Assignee: DePuy Mitek, LLC, Raynham, MA (US)

( * ) Notice: Subject to any disclaimer, the term of this patent is extended or adjusted under 35 U.S.C. 154(b) by 312 days.

This patent is subject to a terminal disclaimer.

(21) Appl. No.: 14/726,589

(22) Filed: May 31, 2015

(65) Prior Publication Data

US 2016/0022263 A1 Jan. 28, 2016

Related U.S. Application Data

(63) Continuation of application No. 11/309,830, filed on Oct. 5, 2006, now Pat. No. 9,072,514.

(51) Int. Cl.
*A61B 17/04* (2006.01)
*A61B 17/06* (2006.01)
*A61B 17/00* (2006.01)

(52) U.S. Cl.
CPC ...... *A61B 17/0485* (2013.01); *A61B 17/0401* (2013.01); *A61B 17/06166* (2013.01);
(Continued)

(58) Field of Classification Search
CPC .................. A61B 17/0485; A61B 17/06166
See application file for complete search history.

(56) References Cited

U.S. PATENT DOCUMENTS

| | | | |
|---|---|---|---|
| 2,054,149 A | 9/1936 | Wappler | |
| 2,167,080 A | 7/1939 | Mason | |

(Continued)

FOREIGN PATENT DOCUMENTS

| | | |
|---|---|---|
| GB | 792678 A | 4/1958 |
| JP | 3-295551 B2 | 12/1991 |

(Continued)

OTHER PUBLICATIONS

Yian et al. "Arthroscopic Repair of SLAP Lesions with a Bioknotless Suture Anchor", Arthroscopy: The Journal of Arthroscopic and Related Surgery, vol. 20, No. 5 May-Jun. 2004: pp. 547-551.

*Primary Examiner* — Alexander Orkin
(74) *Attorney, Agent, or Firm* — Patent Law Offices of Michael E. Woods; Michael E. Woods

(57) ABSTRACT

A member of a rigid flexible elastic material, the member including a body portion and an aperture portion with the member adapted for delivery through an axial longitudinal channel of a percutaneous delivery subsystem, the aperture portion including an expanded mode having a lateral dimension greater than an inner diameter of the channel when the aperture portion extends outside the channel and a collapsed mode wherein the lateral dimension is not greater than the inner diameter of the channel when the aperture portion is within the channel, the channel including a first axial opening and a second axial opening with the aperture portion transitioning from the expanded mode to the collapsed mode when inserted into the openings and the aperture transitioning from the collapsed mode to the expanded mode when exiting from the openings.

45 Claims, 15 Drawing Sheets

(52) U.S. Cl.
CPC ........... *A61B 17/06066* (2013.01); *A61B 2017/00867* (2013.01); *A61B 2017/061* (2013.01)

(56) References Cited

U.S. PATENT DOCUMENTS

| | | |
|---|---|---|
| 2,448,432 A | 8/1948 | Huning |
| 2,567,408 A | 9/1951 | Soderberg |
| 2,716,515 A | 8/1955 | Moghadam |
| 3,791,387 A | 2/1974 | Itoh |
| 3,805,791 A | 4/1974 | Seuberth et al. |
| 3,828,790 A | 8/1974 | Curtiss et al. |
| 3,987,839 A | 10/1976 | Pace |
| 4,011,658 A | 3/1977 | Tarrson et al. |
| 4,102,478 A | 7/1978 | Samoilov |
| 4,133,339 A | 1/1979 | Naslund |
| 4,326,530 A | 4/1982 | Fleury, Jr. |
| 4,347,846 A | 9/1982 | Dormia |
| 4,641,652 A | 2/1987 | Hutterer et al. |
| 4,667,860 A | 5/1987 | Feuerman |
| 4,779,616 A | 10/1988 | Johnson |
| 5,084,054 A | 1/1992 | Bencini et al. |
| 5,100,418 A | 3/1992 | Yoon et al. |
| 5,251,797 A | 10/1993 | Martin |
| 5,281,237 A | 1/1994 | Gimpelson |
| 5,454,834 A | 10/1995 | Boebel et al. |
| 5,496,330 A | 3/1996 | Bates et al. |
| 5,499,991 A | 3/1996 | Garman et al. |
| 5,501,692 A | 3/1996 | Riza |
| 5,522,819 A | 6/1996 | Graves et al. |
| 5,561,973 A | 10/1996 | St Germain |
| 5,573,530 A | 11/1996 | Fleury et al. |
| 5,618,290 A | 4/1997 | Toy et al. |
| 5,628,756 A | 5/1997 | Barker, Jr. et al. |
| 5,643,292 A | 7/1997 | Hart |
| 5,722,981 A | 3/1998 | Stevens |
| 5,755,728 A | 5/1998 | Maki |
| 5,836,955 A | 11/1998 | Buelna et al. |
| 5,895,395 A | 4/1999 | Yeung |
| 5,906,624 A | 5/1999 | Wenstrom, Jr. |
| 5,947,979 A | 9/1999 | Ouchi et al. |
| 5,976,073 A | 11/1999 | Ouchi |
| 6,013,086 A | 1/2000 | Ouchi et al. |
| 6,015,381 A | 1/2000 | Ouchi |
| 6,022,360 A | 2/2000 | Reimels et al. |
| 6,077,277 A | 6/2000 | Mollenauer et al. |
| 6,090,129 A | 7/2000 | Ouchi |
| 6,093,195 A | 7/2000 | Ouchi |
| 6,132,440 A | 10/2000 | Hathaway et al. |
| 6,136,010 A | 10/2000 | Modesitt et al. |
| 6,143,017 A | 11/2000 | Thal |
| 6,152,922 A | 11/2000 | Ouchi |
| 6,187,017 B1 | 2/2001 | Gregory, Jr. |
| 6,217,589 B1 | 4/2001 | McAlister |
| 6,224,611 B1 | 5/2001 | Ouchi |
| 6,245,078 B1 | 6/2001 | Ouchi |
| 6,299,612 B1 | 10/2001 | Ouchi |
| 6,402,761 B2 | 6/2002 | McAlister |
| 6,423,054 B1 | 7/2002 | Ouchi |
| 6,423,060 B1 | 7/2002 | Ouchi |
| 6,439,000 B1 | 8/2002 | Smark |
| 6,471,690 B1 | 10/2002 | Ouchi |
| 6,475,229 B1 | 11/2002 | Pagedas |
| 6,517,539 B1 | 2/2003 | Smith et al. |
| 6,517,551 B1 | 2/2003 | Driskill |
| 6,554,845 B1 | 4/2003 | Fleenor et al. |
| 6,605,096 B1 | 8/2003 | Ritchart |
| 6,629,984 B1 | 10/2003 | Chan |
| 6,723,107 B1 | 4/2004 | Skiba et al. |
| 6,761,717 B2 | 7/2004 | Bales et al. |
| 6,814,740 B2 | 11/2004 | McAlister |
| 6,860,887 B1 | 3/2005 | Frankle |
| 6,972,017 B2 | 12/2005 | Smith et al. |
| 6,991,636 B2 | 1/2006 | Rose |
| 7,276,067 B2 | 10/2007 | Bales et al. |
| 7,387,632 B2 | 6/2008 | Ouchi |
| 7,402,162 B2 | 7/2008 | Ouchi |
| 7,458,973 B2 | 12/2008 | Ouchi |
| 8,282,658 B2 | 10/2012 | Knapp et al. |
| 8,579,923 B2 | 11/2013 | Knapp |
| 9,072,514 B2 | 7/2015 | Knapp et al. |
| 2001/0002436 A1* | 5/2001 | Bowman ............ A61B 17/0469 606/232 |
| 2001/0012945 A1 | 8/2001 | Romano |
| 2001/0016747 A1 | 8/2001 | Romano et al. |
| 2002/0107526 A1 | 8/2002 | Greenberg et al. |
| 2002/0107530 A1 | 8/2002 | Sauer et al. |
| 2002/0156344 A1* | 10/2002 | Pasricha ............ A61B 1/0014 600/113 |
| 2002/0165555 A1 | 11/2002 | Stein et al. |
| 2003/0195528 A1 | 10/2003 | Ritchart |
| 2003/0236535 A1 | 12/2003 | Onuki et al. |
| 2004/0010273 A1 | 1/2004 | Diduch et al. |
| 2004/0097975 A1 | 5/2004 | Rose |
| 2004/0127915 A1 | 7/2004 | Fleenor et al. |
| 2004/0236353 A1 | 11/2004 | Bain et al. |
| 2005/0033365 A1 | 2/2005 | Courage |
| 2005/0038449 A1 | 2/2005 | Sancoff et al. |
| 2005/0043746 A1 | 2/2005 | Pollak et al. |
| 2005/0065535 A1 | 3/2005 | Morris et al. |
| 2005/0096650 A1 | 5/2005 | Ouchi |
| 2005/0101967 A1 | 5/2005 | Weber et al. |
| 2005/0131424 A1 | 6/2005 | Ouchi |
| 2005/0277947 A1 | 12/2005 | Ziegler |
| 2006/0067967 A1 | 3/2006 | Bowman et al. |
| 2006/0069399 A1 | 3/2006 | Weisel et al. |
| 2008/0086147 A1 | 4/2008 | Knapp |
| 2008/0086171 A1 | 4/2008 | Knapp et al. |
| 2008/0215064 A1 | 9/2008 | Motosugi |
| 2009/0005792 A1 | 1/2009 | Miyamoto et al. |
| 2009/0018554 A1 | 1/2009 | Thorne et al. |
| 2009/0277934 A1 | 11/2009 | Youngman |
| 2011/0098726 A1 | 4/2011 | Knapp |
| 2011/0098742 A1 | 4/2011 | Knapp et al. |

FOREIGN PATENT DOCUMENTS

| | | |
|---|---|---|
| JP | 4-226643 | 8/1992 |
| JP | 10-277044 | 10/1998 |
| JP | 11-009610 | 1/1999 |
| JP | 11-114059 | 4/1999 |
| JP | 2002540834 A | 12/2002 |
| WO | 3007530 A2 | 2/2000 |
| WO | 2000007530 A2 | 2/2000 |
| WO | 2006023975 A2 | 3/2006 |
| WO | 2008045682 A1 | 4/2008 |
| WO | 2008045683 A1 | 4/2008 |

* cited by examiner

US 9,999,420 B2

SHAPE MEMORY FILAMENT FOR SUTURE MANAGEMENT

CROSS REFERENCE TO RELATED APPLICATIONS

This application is a Continuation of U.S. patent application Ser. No. 11/309,830, now U.S. Pat. No. 9,072,514, filed 5 Oct. 2006, the contents of which are hereby expressly incorporated by reference thereto in its entirety for all purposes.

BACKGROUND OF THE INVENTION

The invention relates generally to surgical suture management and more specifically to a percutaneous suture management system and method, more specifically for suture fixation of tissue, through procedures such as for example open and arthroscopic surgeries.

Arthroscopic suturing techniques and instruments have been developed in order to facilitate the suturing of tissue during arthroscopic surgical procedures. In arthroscopic surgery, access to a surgical work site within a patient's body is normally provided through one or more portals formed directly in the patient's body or through one or more cannulas inserted into the body of a patient through small incisions. A chosen surgical procedure is carried out by a surgeon through the use of elongated instruments inserted through these cannulas and it often becomes necessary to suture selected tissue at the surgical work site.

Since the work site is only accessible through a small portal or cannula and since it is very difficult to tie sutures within the body, various devices and techniques have been developed to enable the surgeon to manipulate sutures arthroscopically. For example, some procedures enable the surgeon to pass suture material through selected tissue, form a surgical knot extracorporeally and then move the knot with a knot pusher through the portal or cannula into position adjacent the desired tissue to be sutured. Some cannula instruments used to pass the suture incorporate a hollow needle provided with some structure, often a wire loop, to guide the suture through the tissue pierced by the needle, with the needle extended through a cannula. It is known to use a non-metallic suture shuttle having loops on opposite ends for passing through the bore of a roller type suture passing device. In some cases, each loop of the suture shuttle includes a short leader portion in the form of a single strand monofilament for threading the suture shuttle through the bore of the elongated instrument. In other cases, the short leader portion is eliminated, and the surgeon must squeeze the leading loop together to insert the shuttle into the bore of the elongated instrument.

These instruments are typically available for use exclusively through the cannula and because cannula placement locations are limited, the ability of a surgeon to place and tie each suture at optimum locations is constrained, both by placement of the cannula as well as limitations of working exclusively through the cannula when placing and tying each suture. For example, when working through a cannula or similar portal, a surgeon may have about forty degrees of freedom from a central axis of the portal in which to locate and place sutures. When it is necessary or desirable to locate sutures outside of this limit, then the surgeon must weigh the disadvantages of adding another portal/cannula in an appropriate location against the advantages of positioning the suture at the optimum location. Sometimes such a suture is not used or it is located sub-optimally because the disadvantages predominate. In instances in which it would be desirable to position or distribute sutures through a wide range of angles, it becomes impractical to use arthroscopic techniques due to the relatively large number of portals/cannulas that are required.

A shape memory alloy (SMA) (also known as memory metal or smart wire) is a metal that remembers its geometry. After it is deformed, it regains its original geometry by itself during heating (one-way effect) or, at higher ambient temperatures, simply during unloading (pseudo-elasticity). Main types of SMA include copper-zinc-aluminum, copper-aluminum-nickel, and nickel-titanium (NiTi) alloys. NiTi alloys are generally more expensive and possess superior mechanical properties when compared to copper-based SMAs. The nickel-titanium alloys were first developed in 1962-1963 by the Naval Ordnance Laboratory and commercialized under the trade name Nitinol (an acronym for Nickel Titanium Naval Ordnance Laboratories). Metal alloys are not the only thermally responsive materials, as shape memory polymers have also been developed, having become commercially available in the late 1990's. There is another type of SMA called ferromagnetic shape memory alloys (FSMA), that change shape under strong magnetic fields. These materials are of particular interest as the magnetic response tends to be quicker and more efficient than temperature-induced responses. Shape memory alloys are able to show an obviously elastic deformation behavior which is called Mechanical Shape Memory Effect or Superelasticity. This deformation can be as high as 20× of the elastic strain of steel.

In surgery, percutaneous pertains to any medical procedure where access to inner organs or other tissue is done via a puncture or a piercing of the skin, rather than by using an "open" approach where inner organs or tissue are exposed (typically with the use of a scalpel or blade to make an incision) or through a cannula or other portal.

What is needed is an apparatus, system, and method for enabling a surgeon to quickly and accurately position a suture at any desired location and optionally along a preferred suture pathway without undue constraint by cannula or other portal systems.

BRIEF SUMMARY OF THE INVENTION

Disclosed is an apparatus, system, and method for percutaneous suture management system that enables an operator to quickly and accurately position a suture at any desired location and optionally along a preferred suture pathway without constraint by cannula or other portal systems. The apparatus includes a member of a rigid flexible elastic material, the member including a body portion and an aperture portion with the member adapted for delivery through an axial longitudinal channel of a percutaneous delivery subsystem, the aperture portion including an expanded mode having a lateral dimension greater than an inner diameter of the channel when the aperture portion extends outside the channel and a collapsed mode wherein the lateral dimension is not greater than the inner diameter of the channel when the aperture portion is within the channel, the channel including a first axial opening and a second axial opening with the aperture portion transitioning from the expanded mode to the collapsed mode when inserted into the openings and the aperture transitioning from the collapsed mode to the expanded mode when exiting from the openings.

A system includes a percutaneous delivery subsystem including a tissue-penetrating member defining an axial longitudinal channel having an internal longitudinal cross-section with the channel including a first longitudinal opening and a second longitudinal opening; and a member of a rigid flexible elastic material, the member including a body portion and an aperture portion with the member adapted for delivery through the axial longitudinal channel, the aperture portion including an expanded mode having a lateral dimension greater than a greatest width of the internal longitudinal cross-section when the aperture portion extends outside the channel and a collapsed mode wherein the lateral dimension is not greater than the greatest width of the channel when the aperture portion is within the channel, with the aperture portion transitioning from the expanded mode to the collapsed mode when inserted into the openings and the aperture transitioning from the collapsed mode to the expanded mode when exiting from the openings.

A method includes a) installing a suture anchor with an attached suture strand in a portion of body adjacent a section of tissue to be secured within a body; b) piercing percutaneously the tissue with a sharp distal end of a spinal needle having a channel extending from the sharp distal end to a proximal end outside the body; c) inserting a member into an end of the spinal needle, the member including a body portion and an aperture portion with the member adapted for delivery through the channel, the aperture portion including an expanded mode having a lateral dimension greater than an inner diameter of the channel when the aperture portion extends outside the channel and a collapsed mode wherein the lateral dimension is not greater than the inner diameter of the channel when the aperture portion is within the channel, the aperture portion transitioning from the expanded mode to the collapsed mode when inserted into the ends and the aperture transitioning from the collapsed mode to the expanded mode when exiting from the ends; d) deploying the aperture portion from the sharp distal end; e) capturing the suture strand with the aperture portion; and f) passing the captured suture strand through the tissue by retracting the aperture portion through the tissue. A method for repairing a superior labrum anterior to posterior tear includes a) installing a posterior portal into a shoulder proximate the superior labrum; b) installing a suture anchor at about a forty-five degree angle into a glenohumeral joint of the shoulder, the suture anchor including at least one suture; c) inserting percutaneously a needle into the shoulder, the needle adjacent a lateral acromion and passing through a supraspinutas tendon of the shoulder; d) introducing a suture transport into the glenohumeral joint through a channel of the needle; e) coupling the suture to the suture transport; and f) extracting the suture transport from the shoulder to extend the suture from the anchor outside the shoulder through the supraspinutas tendon.

Embodiments of the present invention for suture transports are simpler and more efficient than conventional systems for not only passing, delivering, and installing sutures but also to define suture paths through multiple tissue types and/or structures in multiple discrete steps or in one successive procedure as determined by the operator. Embodiments may require fewer portals while providing for a greater angular access area around a portal using small diameter percutaneous piercers that cause less overall trauma and reductions in local trauma, thus promoting quicker and lower risk recoveries.

Systems of the preferred embodiment also enable new procedures while simplifying other procedures as additional uses and applications for the structures are implemented. For example, one preferred embodiment includes a single portal SLAP repair.

BRIEF DESCRIPTION OF THE DRAWINGS

FIG. 5 illustrates a suture transport shown in FIG. 1 used with a percutaneous delivery subsystem;

FIG. 6 illustrates a suture transport extending outside the channel of the spinal needle puncturing the skin portion of a human body, with the aperture of the suture transport shown in the expanded mode;

FIG. 7 illustrates a portion of a shoulder including installation of a suture anchor into a bone of the shoulder near a desired location for a repair of a capsular tissue portion, the suture anchor including four suture strands;

FIG. 8 illustrates the portion of the shoulder shown in FIG. 7 after a percutaneous delivery system pierces both the skin of the shoulder and the capsular tissue at an optimum location and delivers a shuttle transport including an aperture portion through the skin and the capsular tissue;

FIG. 9 illustrates the portion of the shoulder shown in FIG. 7 and FIG. 8 after the shuttle transport is withdrawn through the channel of percutaneous delivery system while the delivery system remains partially within the shoulder but withdrawn from the capsular tissue;

FIG. 10 illustrates the portion of the shoulder shown in FIG. 7, FIG. 8, and FIG. 9 after the shuttle transport is completely withdrawn back through the shoulder with the suture strand extending from an aperture defined by the exiting percutaneous delivery system shown in FIG. 7, FIG. 8, and FIG. 9;

FIG. 13 is a view subsequent to the FIG. 12 view in which a portal is installed into the shoulder segment with a suture anchor and attached suture strand secured into the shoulder through the portal;

FIG. 14 is a view subsequent to the FIG. 13 view in which a percutaneous delivery system has pierced through a skin portion and passed into an interior of the shoulder portion at the desired location while defining a desired suture path through the desired tissue components;

FIG. 15 is a view subsequent to the FIG. 14 view in which a suture transport is delivered from the distal end of the percutaneous delivery system at the desired location;

FIG. 16 is a view subsequent to the FIG. 15 view in which the suture transport is extracted out of the shoulder portion through the portal while the delivery system is retracted;

FIG. 17 is a view subsequent to the FIG. 16 view in which the suture transport has retracted one of the suture strands through the portal and through the suture path defined by the percutaneous delivery system;

DETAILED DESCRIPTION OF THE INVENTION

The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Figure 1:
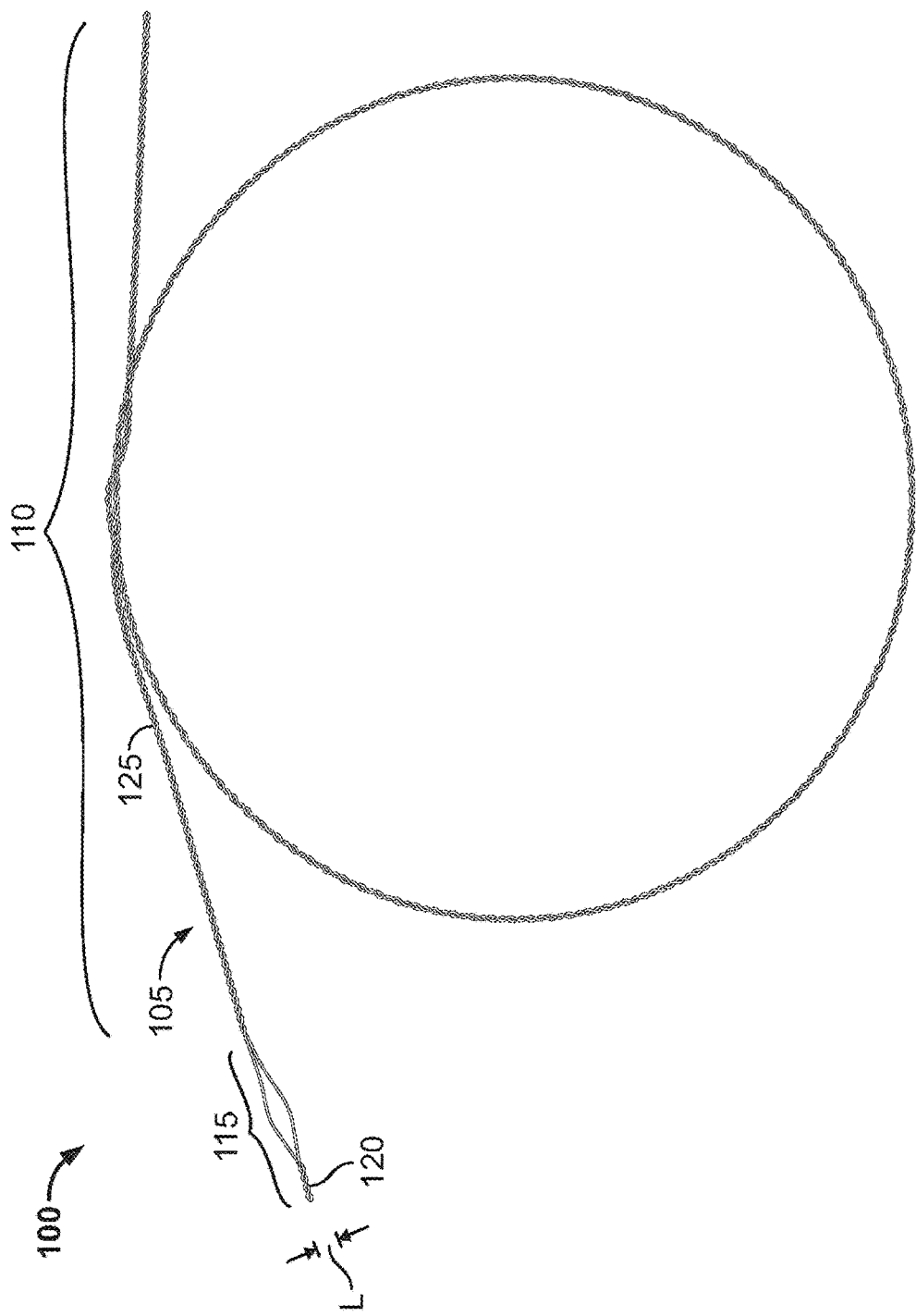
FIG. 1 is a suture transport adapted for percutaneous use according to an embodiment of the present invention.

FIG. 1 is a suture transport 100 adapted for percutaneous use according to an embodiment of the present invention. Transport 100 includes a member 105 of a rigid flexible elastic material, member 105 including a body portion 110 and an aperture portion 115. Member 105 is adapted for delivery through an axial longitudinal channel of a percutaneous delivery subsystem (e.g., an 18 gauge or smaller spinal needle or other skin-piercing delivery system, or the like), with aperture portion 115 including an expanded mode (as shown in FIG. 1) having a lateral dimension (L) greater than an inner diameter of the channel when aperture portion 115 extends outside the channel. The collapsed mode (shown, for example, in FIG. 5) provides for lateral dimension L to be not greater than the inner diameter of the channel when aperture portion 115 is within the channel. The channel includes a first axial opening at a proximal end (closer to the operator of suture transport 100) and a second axial opening at a distal end (closer to the piercing end and typically disposed within the body through a puncture in the skin during use). Aperture portion 115 includes, in the preferred embodiment, a leader element 120 used to load/guide aperture portion 115 into the channel. Leader element 120 may be omitted from some implementations, while in other implementations leader element 120 function is provided in a different manner, such as, for example, to help transition aperture portion 115 from the expanded mode to the collapsed mode, and/or, for example, to help load body member 105 into the channel of the percutaneous delivery subsystem, such as the spinal needle. TABLE I below provides Nominal outside diameter, nominal inside diameter, and nominal wall thicknesses for the specified needle gauge.

TABLE I

Syringe Needle Dimensions

| Needle Gauge | Nominal OD (inches) | Nominal ID (inches) | Nominal Wall Thickness (inches) |
|---|---|---|---|
| 17 | .0580 | .0420 | .0080 |
| 18 | .0500 | .0330 | .0080 |
| 19 | .0420 | .0270 | .0075 |

In the preferred embodiment, body portion 105 is constructed of a single monofilament 125 of rigid memory material (e.g., Nitinol™ other memory material including other metals or polymers, and the like) wound to produce body portion 110, aperture portion 115, and any leader element 120. Body portion 105, including aperture portion 115 in the collapsed mode, is constructed so it passes through an 18 gauge spinal/syringe needle, or smaller diameter needle (larger gauge number). Body portion 105 is sufficiently rigid to be able to be pushed/pulled through the needle channel, and sufficiently elastic that aperture portion 115 repeatedly transitions between the expanded mode and the collapsed mode, permitting multiple uses of one suture transport 100. As long as suture transport 100 is sufficiently rigid and elastic as described above, alternative constructions may be possible. For example, it may not be necessary to use a superelastic material for construction of body 105, as in some cases a precursor alloy may be sufficient. In other instances, a multi-stranded structure may be used in some implementations.

In operation, aperture portion 115 transitions from the expanded mode to the collapsed mode when inserted into either of the channel openings and aperture portion 115 transitions from the collapsed mode to the expanded mode when exiting from any of the channel openings. Suture transport 100 is constructed in such a way that it may be loaded from either end of the channel (e.g., the spinal needle) by inserting either body portion 110 or aperture portion 115. Many conventional systems include a handle or other structure that prevents such bi-directional, multi-option loading. Suture transport 100 of FIG. 1 is specifically constructed without a handle or other structure permitting it to pass entirely through a channel from either end to the other, irrespective of which "end" of suture transport 100 is inserted into which end of the channel.

Figure 2:
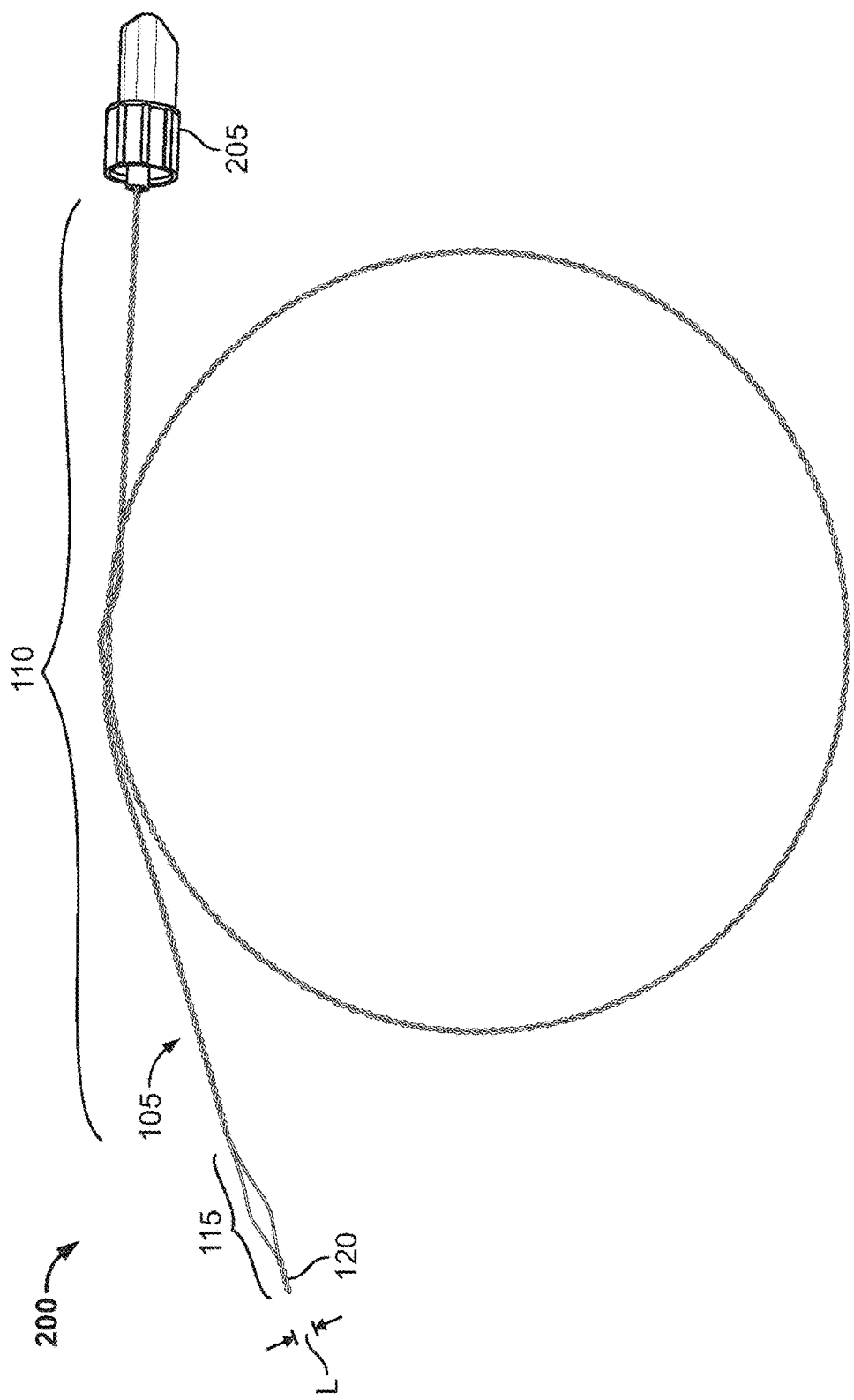
FIG. 2 is a first alternate embodiment of the suture transport shown in FIG. 1.

FIG. 2 is a first alternate embodiment of a suture transport 200. Suture transport 200 includes a handle 205 coupled to the proximal end of body member 105 shown in FIG. 1. While handle 205 inhibits two-way and "either end" loading of suture transport 200 into the percutaneous delivery system, suture transport 200 is beneficial by addition of the handle as that may, in some instances, permit easier insertion or retraction through the channel and/or through tissue of the body, such as for example, enabling easier application of greater axial forces to body member 105. In other respects, suture transport 200 corresponds closely to suture transport shown in FIG. 1 in construction, use, and operation.

Figure 3:
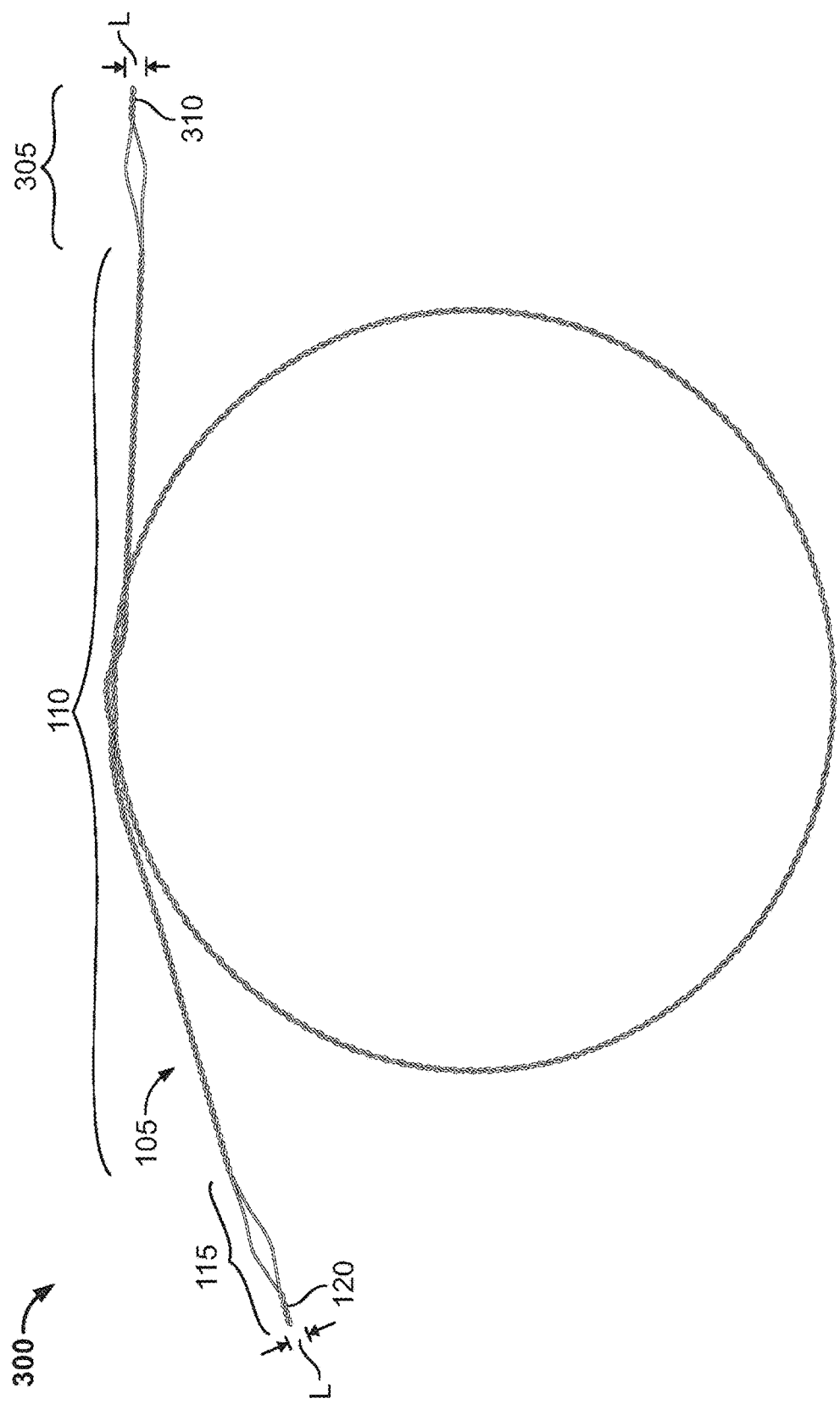
FIG. 3 is a second alternate embodiment of the suture transport shown in FIG. 1.

FIG. 3 is a second alternate embodiment of a suture transport 300. Suture transport 300 includes a second aperture portion 305 coupled to the proximal end of body member 105 shown in FIG. 1. Second aperture portion 305 includes a leader element 310 and also includes an expanded mode with lateral dimension L and a collapsed mode for passage through the channel of percutaneous delivery system. Suture transport 300 permits flexibility in moving sutures or other elements bi-directionally (e.g., it duplicates a sewing motion by eliminating a step, having aperture portions at both ends). In other respects, suture transport 300 corresponds closely to suture transport shown in FIG. 1 in construction, use, and operation.

Figure 4:
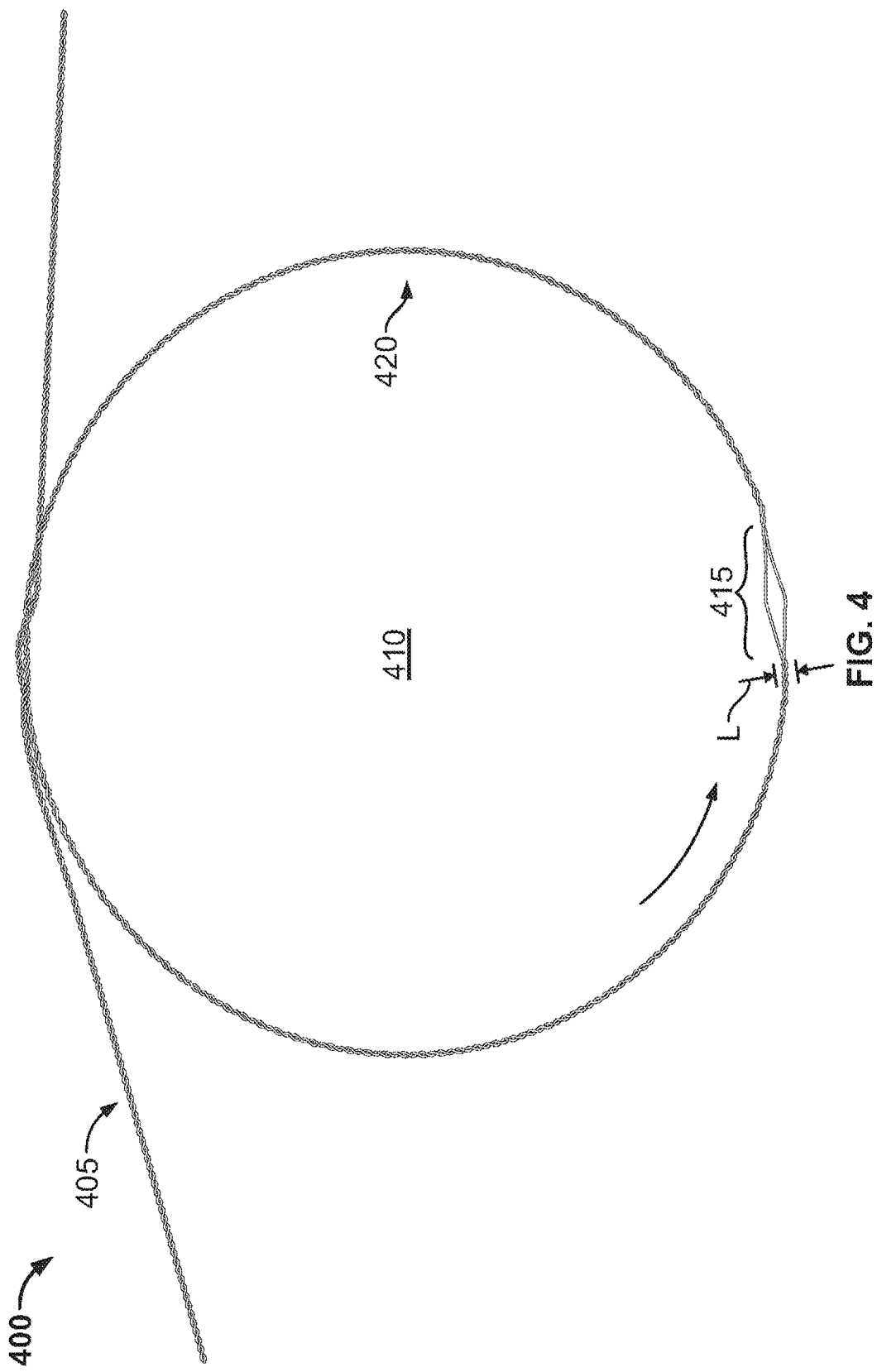
FIG. 4 is a third alternate embodiment of the suture transport shown in FIG. 1.

FIG. 4 is a third alternate embodiment of a suture transport 400. Transport 400 includes a member 405 of a rigid flexible elastic material, member 405 including a first body portion 410, an aperture portion 415, and second body portion 420, aperture portion 415 disposed between the body portions. Member 405 is adapted for delivery through an axial longitudinal channel of a percutaneous delivery subsystem (e.g., an 18 gauge or smaller spinal needle or other skin-piercing delivery system, or the like), with aperture portion 415 including an expanded mode (as shown in FIG. 4) having a lateral dimension (L) greater than an inner diameter of the channel when aperture portion 415 extends outside the channel. One advantage of an implementation such as this is that a suture may be passed without coming out of the skin. In other respects, suture transport 400 corresponds closely to suture transport shown in FIG. 1 in construction, use, and operation.

Figure 5:
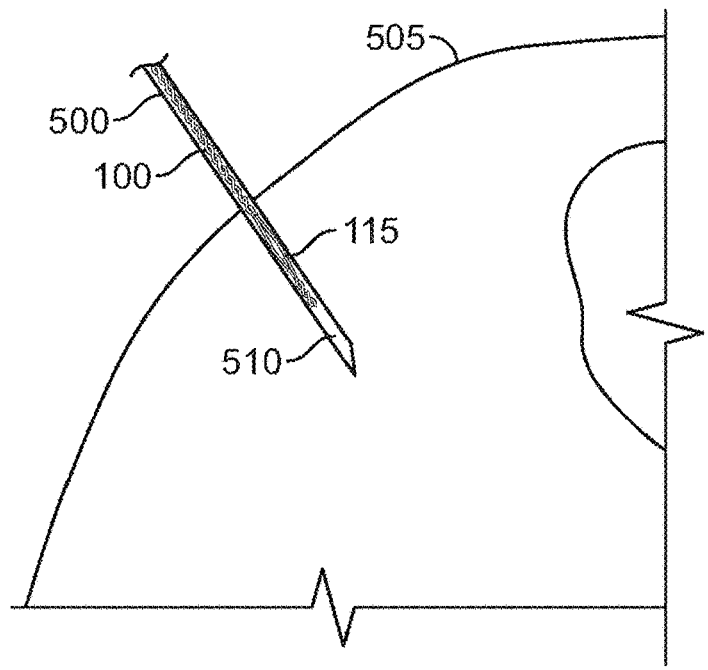
FIG. 5 and FIG. 6 are a sequence of figures illustrating a percutaneous delivery subsystem piercing a portion of a human body (e.g., a shoulder) to deliver one of the suture transports (e.g., the transport of FIG. 1) described herein.
Figure 6:
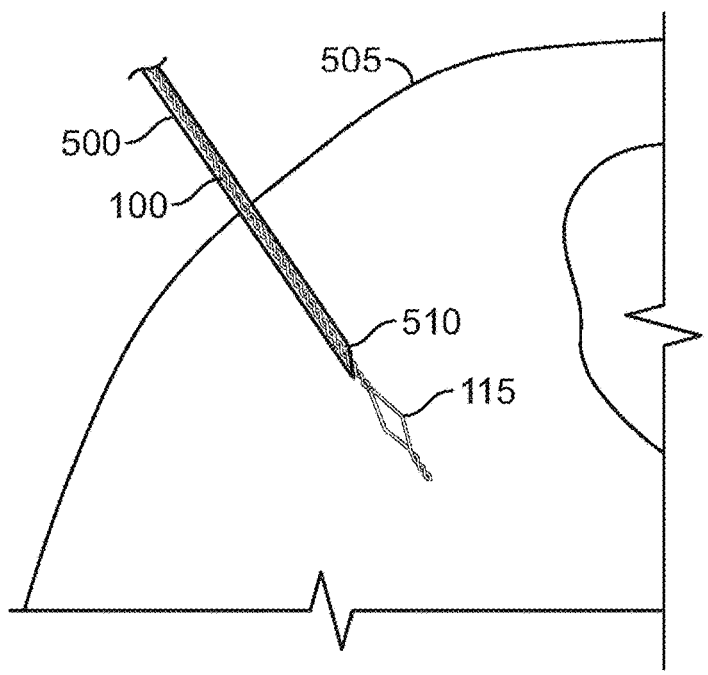

FIG. 5 and FIG. 6 are a sequence of figures illustrating a percutaneous delivery subsystem 500 piercing a portion of a human body 505 (e.g., a shoulder) to deliver one of the suture transports (e.g., transport 100 of FIG. 1) described herein.

FIG. 5 illustrates suture transport 100 shown in FIG. 1 used with subsystem 500. In this example, subsystem 500 includes an 18 gauge or smaller diameter spinal needle having a channel 510. Subsystem 500 is used to deliver the distal end within body 505 to the proper location, including definition of a prospective suture path through various tissue elements within body 505. For example, subsystem 500 may additionally pierce internal tendons, ligaments, and other tissue so that when a suture is captured by the aperture portion and the transport is extended or retracted, the suture also passes through the pierced intermediate tissue elements at the location(s) and in the order defined by subsystem 500. Because subsystem 500 may deliver the distal end to practically any location, through many different types of tissue from virtually any angle or orientation, an operator has almost unlimited options when defining and implementing the optimum suture path and ingress/egress location from body 505. As shown (and as described above) aperture portion 115 is in the collapsed mode when within channel 510.

FIG. 6 illustrates suture transport 100 extending outside channel 510 with aperture portion 115 transitioned to the expanded mode. In the preferred embodiment, aperture portion 115 automatically transitions from the collapsed mode shown in FIG. 5 to the expanded mode shown in FIG. 6 when exiting from the distal end of channel 510 because of the construction and configuration of the transports as described herein. When the transport includes one of the handleless embodiments described herein, after delivering aperture portion 115 to the desired location through the optimum path in body 505, subsystem 500 may be withdrawn from body 505, leaving transport 100 in place. Thus, a suture need not pass through delivery subsystem 500 when exiting body 505.

Figure 7:
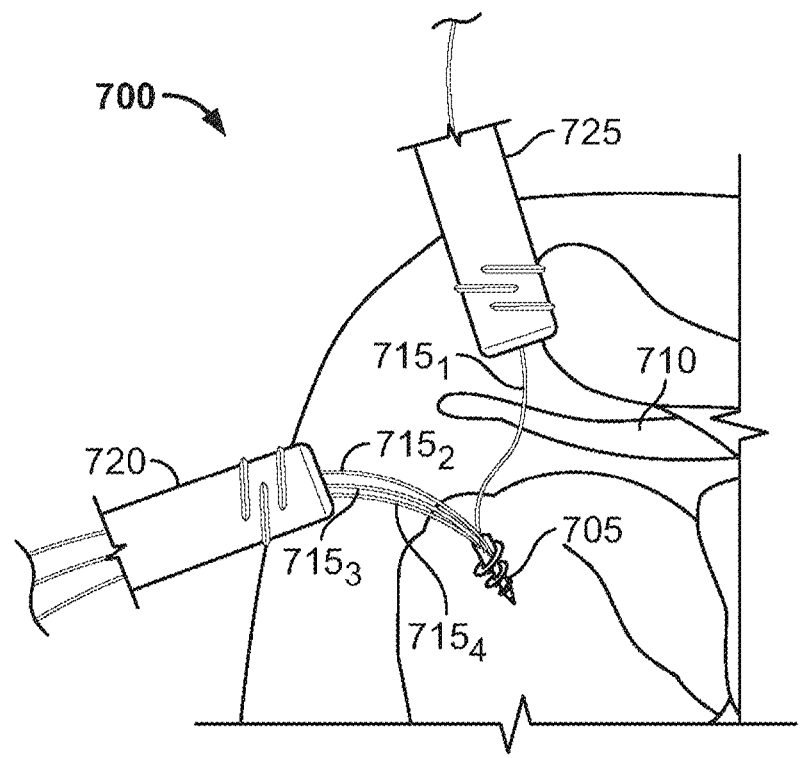
FIG. 7 through FIG. 10 are a detailed sequence of figures illustrating results of use of a percutaneous delivery subsystem piercing a portion of a human body (e.g., a shoulder) to deliver one of the suture transports (e.g., the transport of FIG. 1) described herein.

FIG. 7 through FIG. 10 are a detailed sequence of figures illustrating results of use of a percutaneous delivery subsystem piercing a portion of a human body (e.g., a shoulder) to deliver one of the suture transports (e.g., the transport of FIG. 1) described herein;

FIG. 7 illustrates a portion of a shoulder 700 including installation of a suture anchor 705 into a bone of the shoulder near a desired location for a repair of a capsular tissue portion 710, suture anchor 705 including four suture strands $715_n$. Suture anchor 705 is installed through a first portal 720 and a first suture strand $715_1$ is retrieved through a second portal 735. A gripper, forceps, or other arthroscopic tool/accessory may be used to retrieve a suture strand $715_x$ through second portal 725.

Figure 8:
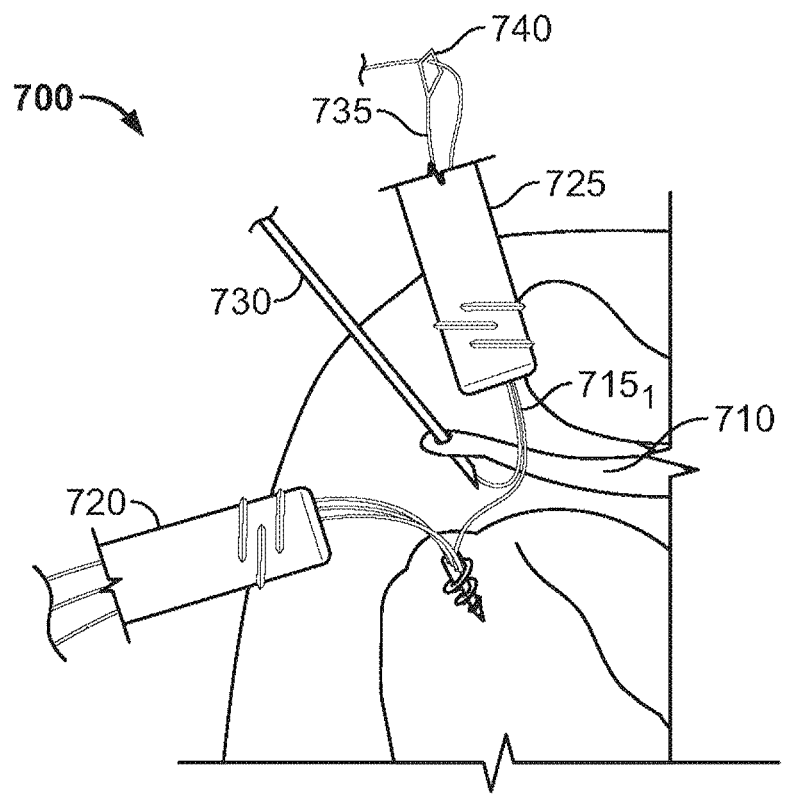

FIG. 8 illustrates the portion of shoulder 700 shown in FIG. 7 after a percutaneous delivery system 730 pierces both the skin of shoulder 700 and capsular tissue 710 at an optimum location and delivers a shuttle transport 735 including aperture portion 740 through the skin and capsular tissue 710. Additionally, aperture portion 740 has been retrieved through second portal 725 in the same or similar manner as suture strand $715_1$ was retrieved. Suture strand $715_1$ is threaded through aperture portion 740 while aperture 740 extends outside shoulder 700 through second portal 725.

Figure 9:
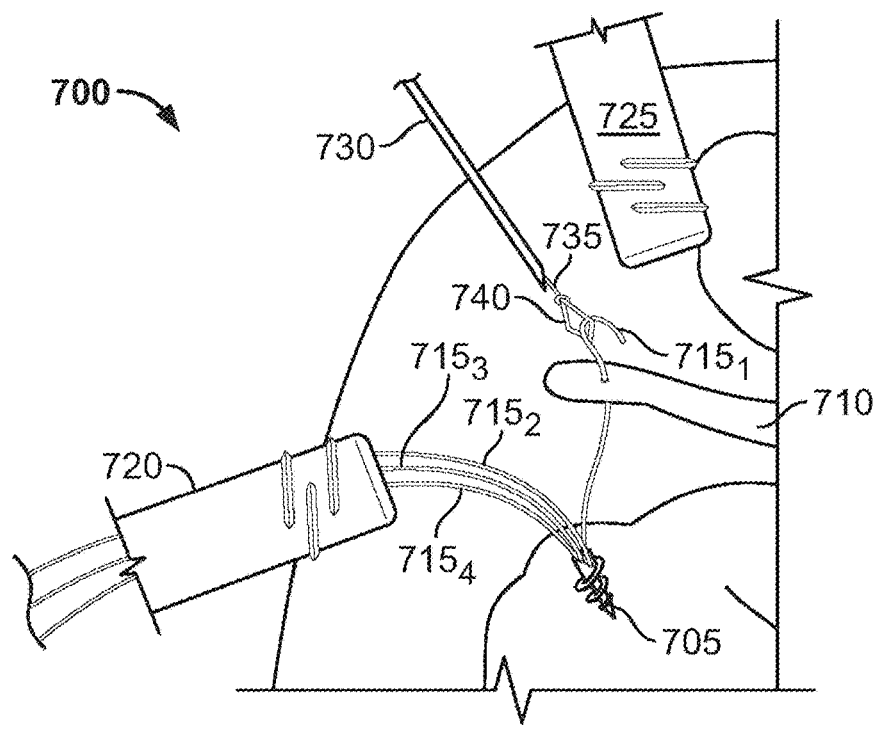

FIG. 9 illustrates the portion of shoulder 700 shown in FIG. 7 and FIG. 8 after shuttle transport 735 is withdrawn through the channel of percutaneous delivery system 730 while system 730 remains partially within shoulder 700 but withdrawn from capsular tissue 710. This demonstrates another feature of the preferred embodiments, namely that the distal end of percutaneous delivery system 730 may be progressively advanced or withdrawn to aid in movement of suture transport 735 within shoulder 700 and the portals and preferred suture installation path(s). For example, depending upon the needs and preferences of the operator, the distal end of percutaneous delivery system 730 may aid in directing suture transport 735 during its movement. That is, the distal may remain positioned through capsular tissue 710 as suture transport (along with suture strand $715_1$) is withdrawn back into second portal 725 towards the exit point of the distal end through capsular tissue 710. After passing suture transport 735 back into shoulder 700 through second portal 725, the distal end of system 730 may be withdrawn from capsular tissue 710 and then suture transport 735 withdrawn through capsular tissue 710 where the distal end passed through. Withdrawing suture transport 735 through capsular tissue 710 also pulls suture strand $715_1$ through capsular tissue 710 along the path defined by delivery system 730 as suture strand $715_1$ is threaded through aperture 740. In some cases, it may not be necessary to progressively withdraw system 730 as suture transport 735 advances along the desired path. The embodiments of the present invention provide this flexibility.

Figure 10:
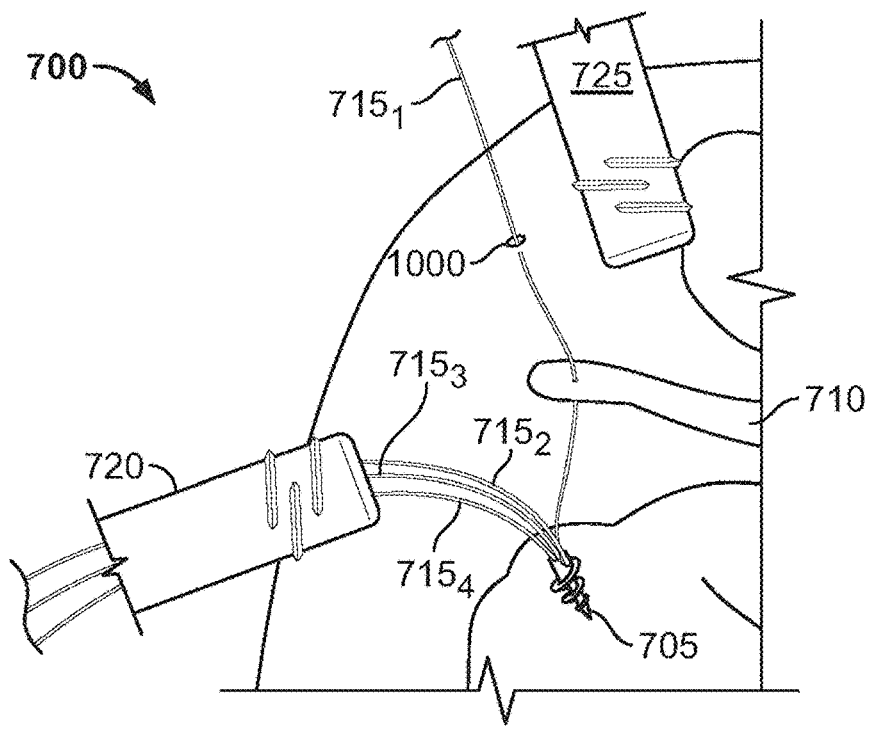

FIG. 10 illustrates the portion of shoulder 700 shown in FIG. 7, FIG. 8, and FIG. 9 after shuttle transport 735 is completely withdrawn through shoulder 700 with suture strand $715_1$ extending from an aperture 1000 defined by the exiting percutaneous delivery system 730 shown in FIG. 7, FIG. 8, and FIG. 9. Suture strand $715_1$ is thus accurately located, positioned, and installed at the appropriate locations in capsular tissue 710 and through aperture 1000.

Figure 11:
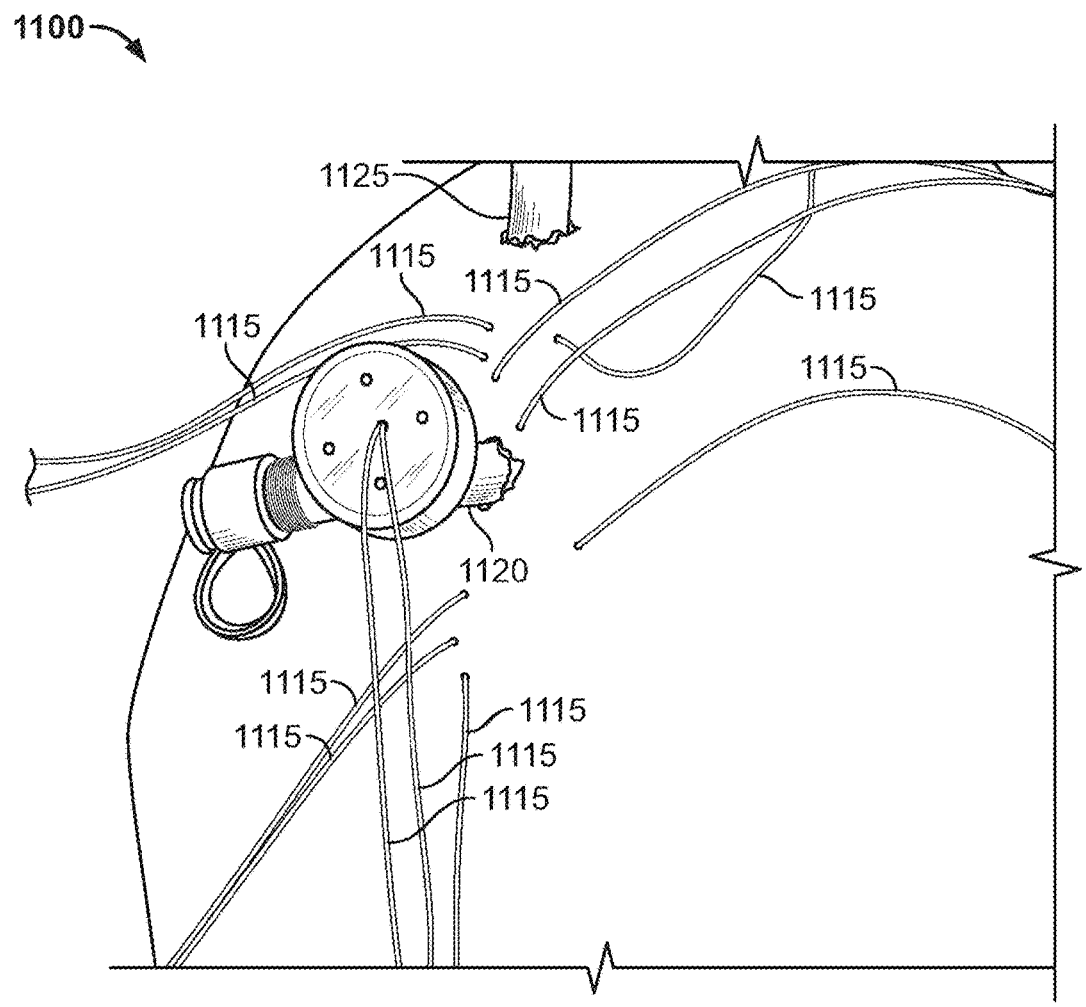
FIG. 11 is an external view of the portion of a body (e.g., a shoulder portion) after optimum placement of multiple suture strands using one or more suture transports described herein in cooperation with a first portal and a second portal as described herein.

FIG. 11 is an external view of the portion of a body 1100 (e.g., a shoulder segment) after optimum placement of multiple suture strands $1115_n$ using one or more suture transports described herein in cooperation with a first portal 1120 and a second portal 1125 as described herein. FIG. 11 illustrates some of the advantages of the present invention including 360° suture strand 1115 placement with minimum use of portals. With the two portals shown, it is noted that suture strand 1115 placement is not limited to locations between the two portals, nor within a narrow angular range. Thus the tissue (tendons, ligaments, other cartilage or tissue or the like) to be stabilized may be accessed at virtually any location from virtually any direction and any part of the body portion similarly may be pierced from virtually any direction providing great flexibility in installing one or more suture strands in the optimum number, locations, and directions.

The following discusses use of preferred embodiments of the suture transport for demonstrating preparation of a set of sutures for a SLAP procedure as applied to repairing shoulder instability. The preparation for this arthroscopic repair of a shoulder begins by installing a suture anchor (e.g., in a portion of bone), at a point where a portion of capsular tissue is desired to be fixed. Initially, some number of strands of suture material attached to the suture anchor is passed through a first portal with the anchor prior to installation. Each strand is passed through the portion of the capsular tissue. The procedures of the preferred embodiments may be achieved in different modalities—suture strands may be installed in multiple discrete steps (e.g., successive retrieval of the suture strand in two stages—first through the capsular tissue and then second through the skin covering the shoulder portion). The embodiments of the present invention optionally provides for such multiple stages to be achieved in a single integrated step. That is, a percutaneous delivery system pierces the shoulder and the capsular tissue in one step and delivers the distal end of the delivery system proximate the suture anchor, once for each suture strand. The suture transport is passed through the channel of the delivery system so that the aperture portion is available to be loaded with the suture strand in question. The delivery system is retracted, and then the suture transport delivers the suture strand through the capsular tissue and the shoulder when retracted. Of course, the present invention permits use of the two stage when necessary or desirable by first locating each suture strand appropriately through the capsular tissue and then, later, retrieving each strand through the shoulder. The present invention provides a great degree of flexibility, not just with locating and delivering a suture strand, but also in combining or separating steps of many arthroscopic procedures used for tissue stabilization. Each suture strand is passed through a portion of the skin of a body part, such as for example a shoulder, each suture strand accurately, independently, and optimally installed with a minimal number of portals installed. At this point, arthroscopic knots are tied and advanced in the normal fashion.

The present invention may be used in a number of surgical procedures involved with tissue tying (e.g., arthroscopic and open surgeries), such as rotator cuff repair or shoulder instability repair among other types of procedures in which cartilage (tendons, ligaments, and the like) and other tissue are stabilized and secured.

Figure 12:
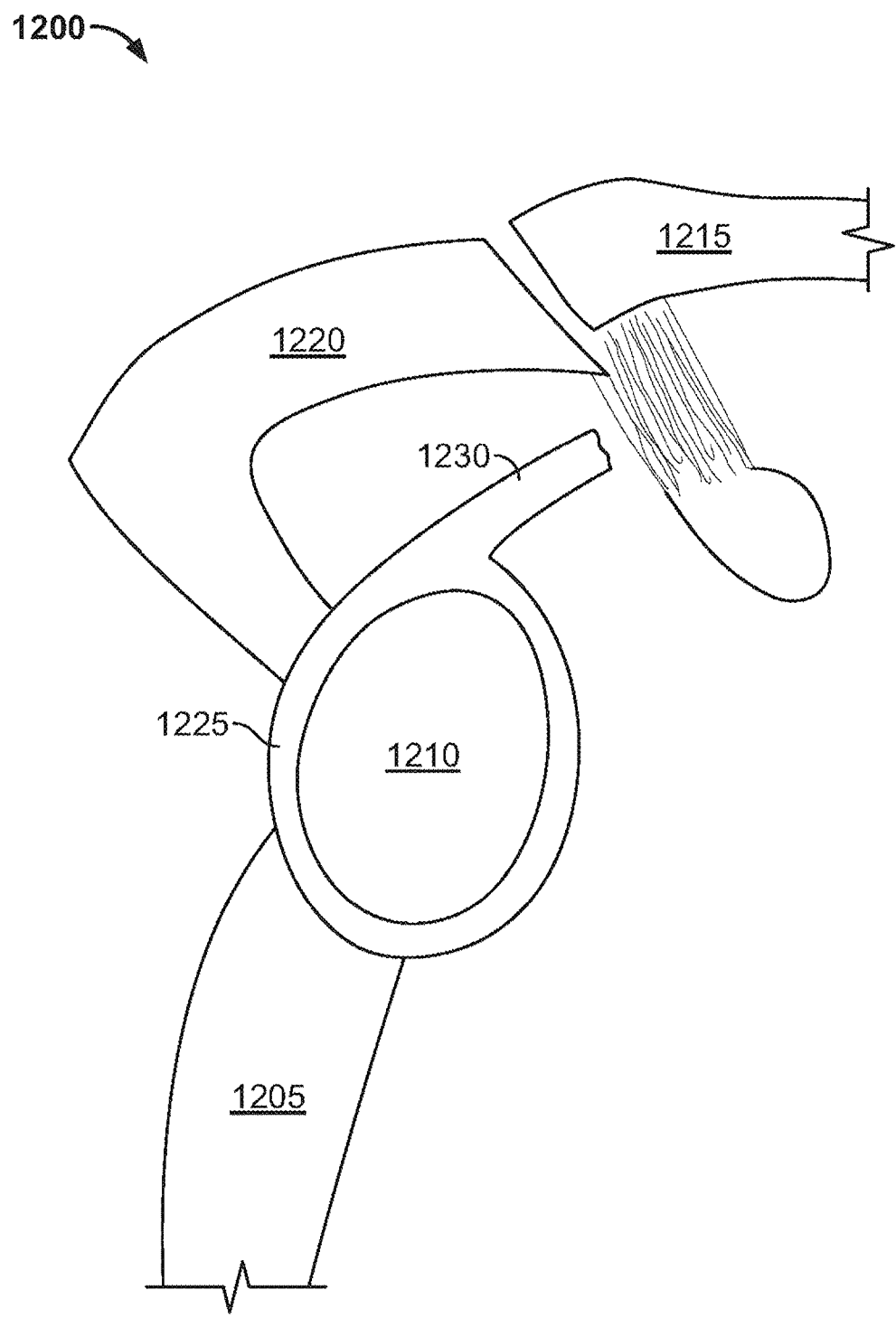
FIG. 12 is side view of a shoulder portion.

FIG. 12 is side view of a shoulder 1200. At one level, shoulder 1200 is a ball and socket joint. An upper part of a humerus 1205 includes a ball that fits into a socket portion of a scapula called a glenoid 1210. Shoulder 1200 is made up of three bones: the scapula (shoulder blade), humerus 1205 (upper arm bone) and a clavicle (collarbone) 1215. A part of the scapula that makes up the roof of the shoulder is called an acromion 1220. A rotator cuff is responsible for the motion, stability, and power of humerus 1205.

A joint where acromion 1220 and clavicle 1215 join together is known as an acromioclavicular (AC) joint. There are ligaments that provide stability to this joint. The true shoulder joint is called a glenohumeral joint and is formed by humerus (upper arm) 1205 and a glenoid labrum 1225 of the scapula (shoulder blade). The relative size of these two structures is analogous to a golf ball (head of the humerus) on a golf tee (glenoid). This makes the shoulder joint have a large range of. This large range of motion also contributes to injuries. One type of injury is the SLAP lesion. Labrum 1225 deepens the golf tee to help make the shoulder more stable. A biceps tendon 1230 attaches at the top of labrum 1225. This is the area of the SLAP lesion. SLAP is an acronym for Superior Labrum Anterior to Posterior. This describes the way the labrum tears.

The following is a description of a preferred embodiment for a novel SLAP repair making use of a suture transport as described herein. The glenohumeral joint, subacromial space and proposed portals are injected with a combination of lidocaine and Marcaine with epinephrine after attempting to aspirate prior to injecting. A standard posterior portal is opened using a #15 blade taking care to place the incisions in the Langer lines. A blunt obturator is used to enter the shoulder. The 4 mm 30 degree arthroscope is placed in the shoulder and an anterior portal is opened using inside-out technique. A thorough diagnostic arthroscopy is performed.

A lateral portal is not necessary for this type of repair. The posterior portal is used for viewing and the anterior portal is the working portal. The superior labral tear is identified. The glenoid is cleaned down to bleeding cortical bone using an arthroscopic elevator, rasp and a motorized shaver. An arthroscopic awl is frequently used to assure a good bleeding surface.

A drill guide is brought in to the glenohumeral joint through the anterior portal, passed medial to the long head of the biceps tendon and placed on the posterosuperior glenoid at a 45° angle. The drill is placed and bottomed out on the guide and removed. Without moving the guide, an anchor is placed and tapped into position until the handle bottoms out on the guide. Multiple counterclockwise turns are performed with the handle to allow the insertor to be removed. The suture ends are smartly tugged to set the anchor. An 18 gauge spinal needle is brought into the shoulder percutaneously adjacent to the lateral acromion. It is seen to enter the shoulder through the supraspinatus tendon. The transport is then introduced through the needle until it enters the glenohumeral joint. A grasper is used to capture the transport and it is withdrawn through the anterior cannula. The needle is then pulled back through the skin. The two suture ends are passed through the loop end (aperture portion) of the transport and the transport is removed leaving the suture exiting through the skin. The suture end closest to the labrum is pulled back through the anterior cannula using a grasper.

Through a percutaneous Nevaiser portal the spinal needle is seen to enter the shoulder behind the biceps tendon. When the capsule is tight in this area an arthroscopic probe can be used to pull the capsule medially for better visualization. The spinal needle is directed under the labrum and seen to exit between the labrum and the glenoid. The transport is introduced through the needle and withdrawn through the anterior cannula. The spinal needle is backed out through the skin. The suture limb is passed through the loop end and the transport is withdrawn leaving the suture through the skin. This is the post for tying. The 2 suture limbs are captured and pulled out through the anterior cannula with both limbs passing medial to the biceps tendon. The sutures are tied using a sliding knot followed by half hitches. The excess sutures are cut using an arthroscopic knot cutter.

An anterosuperior anchor is then placed. The suture ends are again withdrawn in a percutaneous manner laterally. The post suture is retrieved through the anterior cannula. The spinal needle is brought into the shoulder through the subclavicular region. This is just medial and superior to the anterior cannula. The transport is introduced and brought out through the anterior cannula and the needle is backed out of the skin. The post suture limb is passed. Both suture limbs are captured and brought out through the anterior cannula. The sutures are tied and cut. The integrity of the repair is assessed.

FIG. 13 through FIG. 17 are a sequence of views illustrating portions of the SLAP repair described above using a suture transport according to a preferred embodiment of the present invention.

Figure 13:
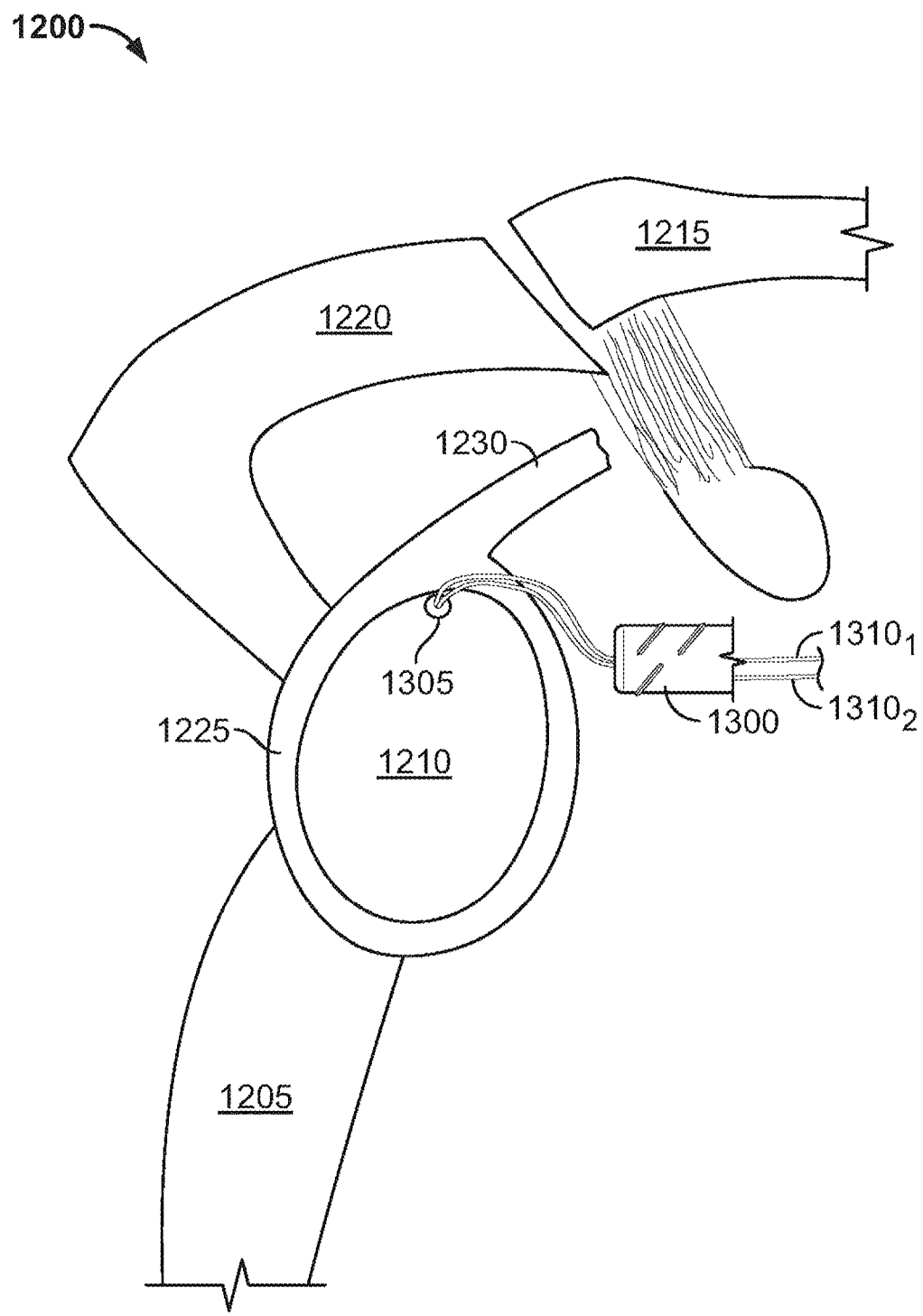
FIG. 13 through FIG. 17 are a sequence of views illustrating a SLAP repair using a suture transport according to a preferred embodiment of the present invention.

FIG. 13 is a view subsequent to the FIG. 12 view in which a portal 1300 is installed into shoulder 1200 with a suture anchor 1305 and attached suture strands 1310 secured into the posterosuperior glenoid 1210 at the 45° angle.

Figure 14:
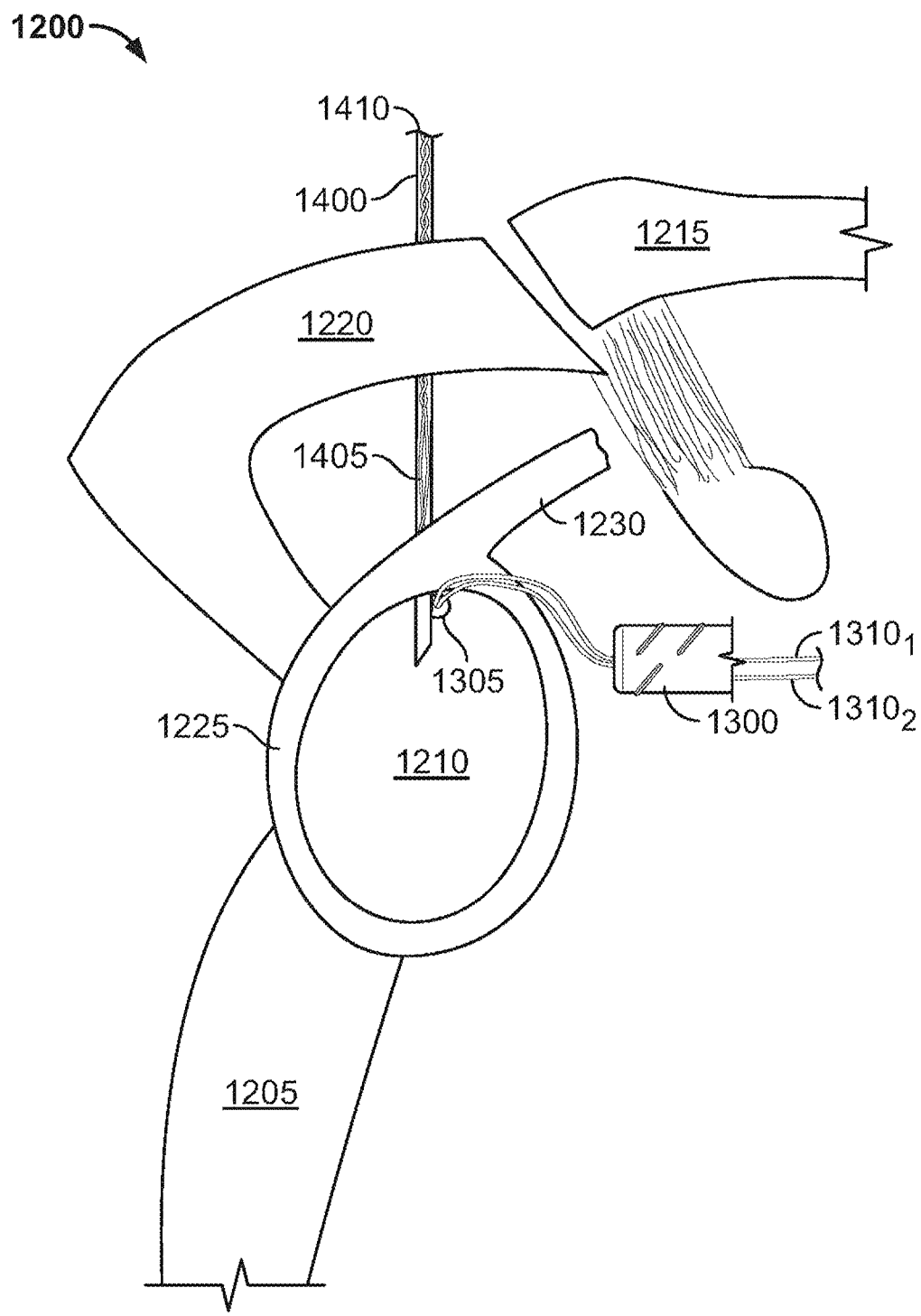

FIG. 14 is a view subsequent to the FIG. 13 view in which a percutaneous delivery system 1400 for a suture transport 1405 has pierced through a skin portion 1410 and passed into an interior of the shoulder portion adjacent to the lateral acromion while defining a desired suture path through the desired tissue components (for example in this case, from skin portion 1410 through the supraspinatus tendon).

Figure 15:
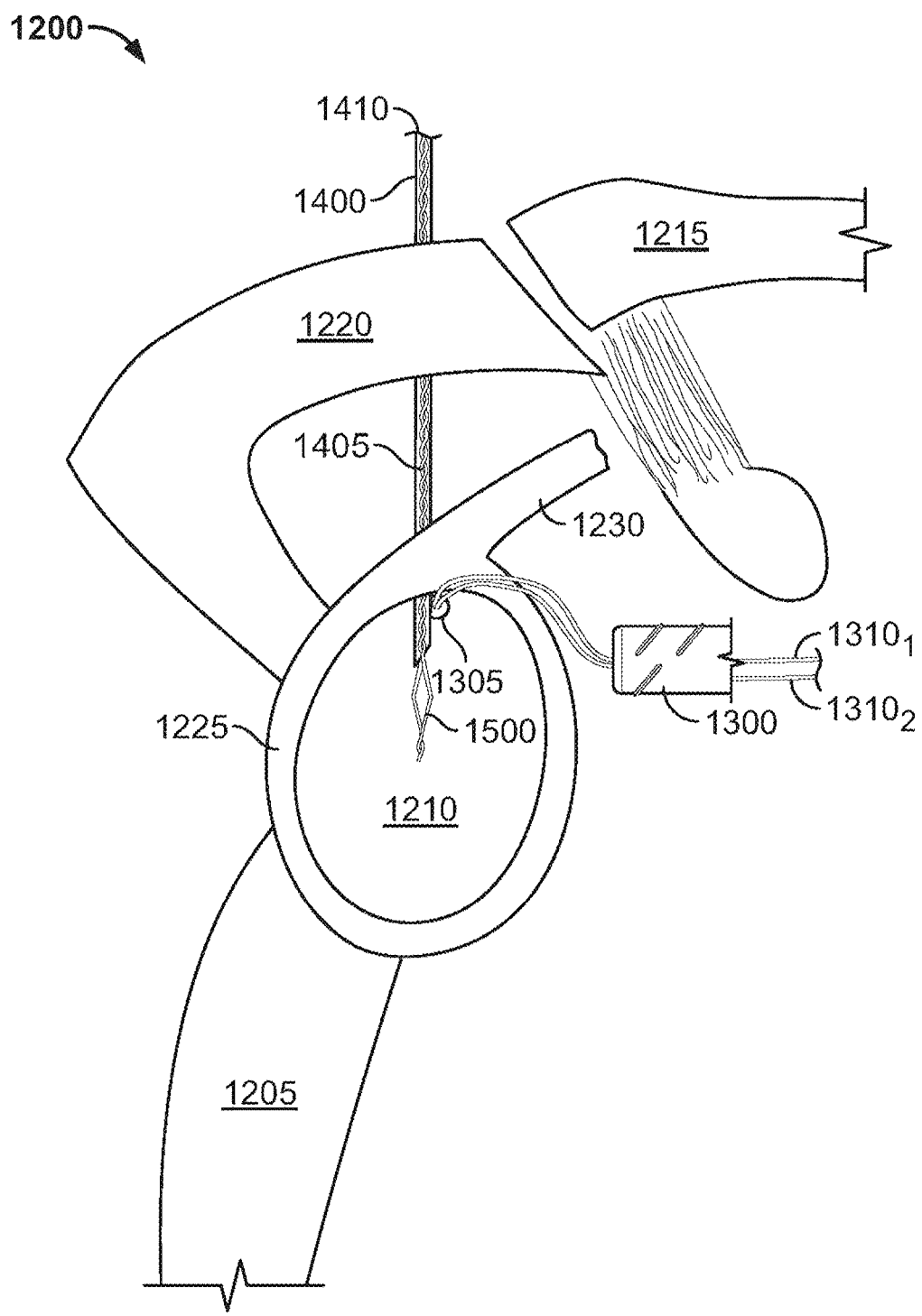

FIG. 15 is a view subsequent to the FIG. 14 view in which an aperture portion 1500 of suture transport 1405 is delivered from the distal end of percutaneous delivery system 1400 at the desired location (for example, into the glenohumeral joint).

Figure 16:
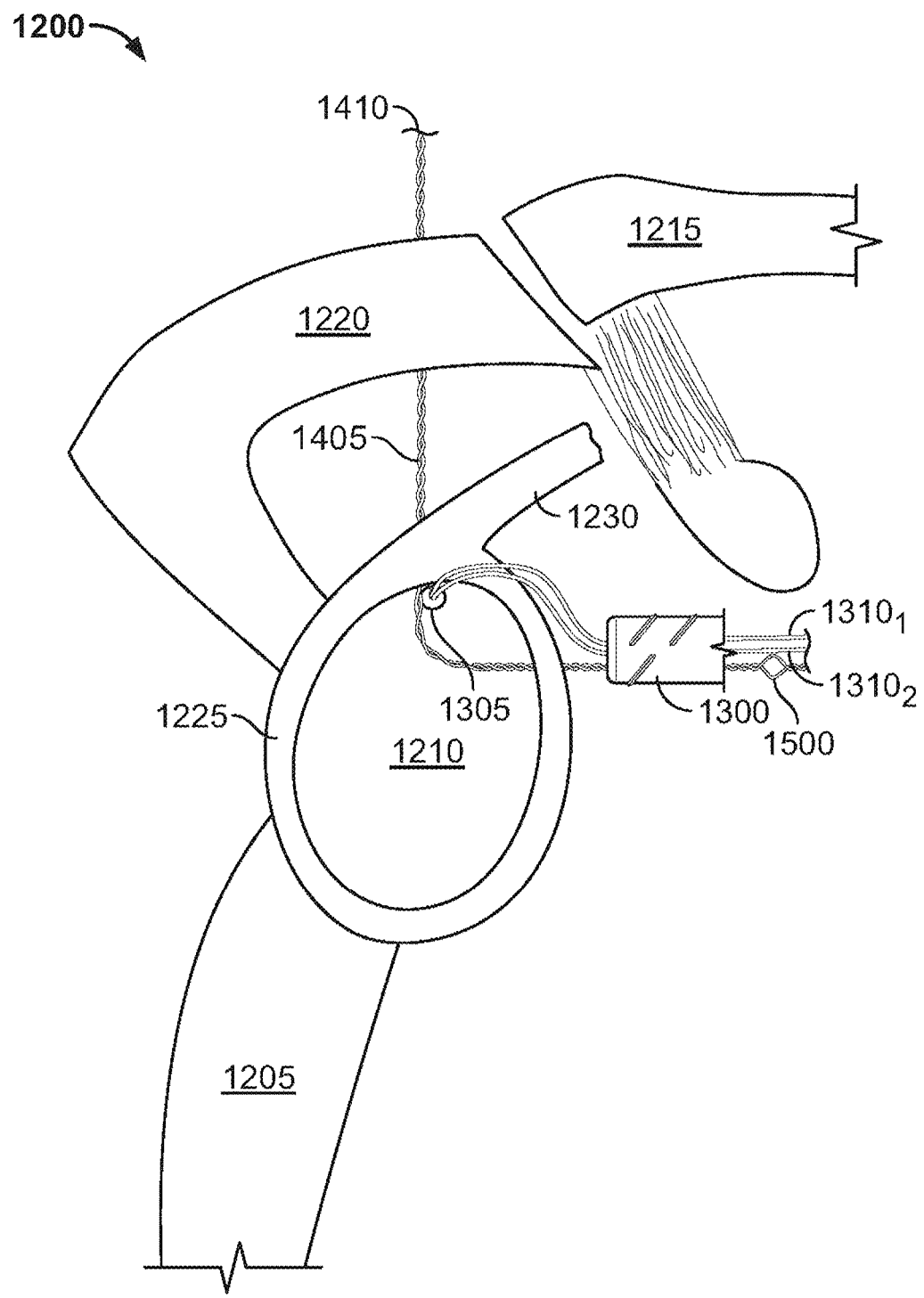

FIG. 16 is a view subsequent to the FIG. 15 view in which suture transport 1405 is extracted out of shoulder 1200 through portal 1300 while the delivery system is retracted.

Figure 17:
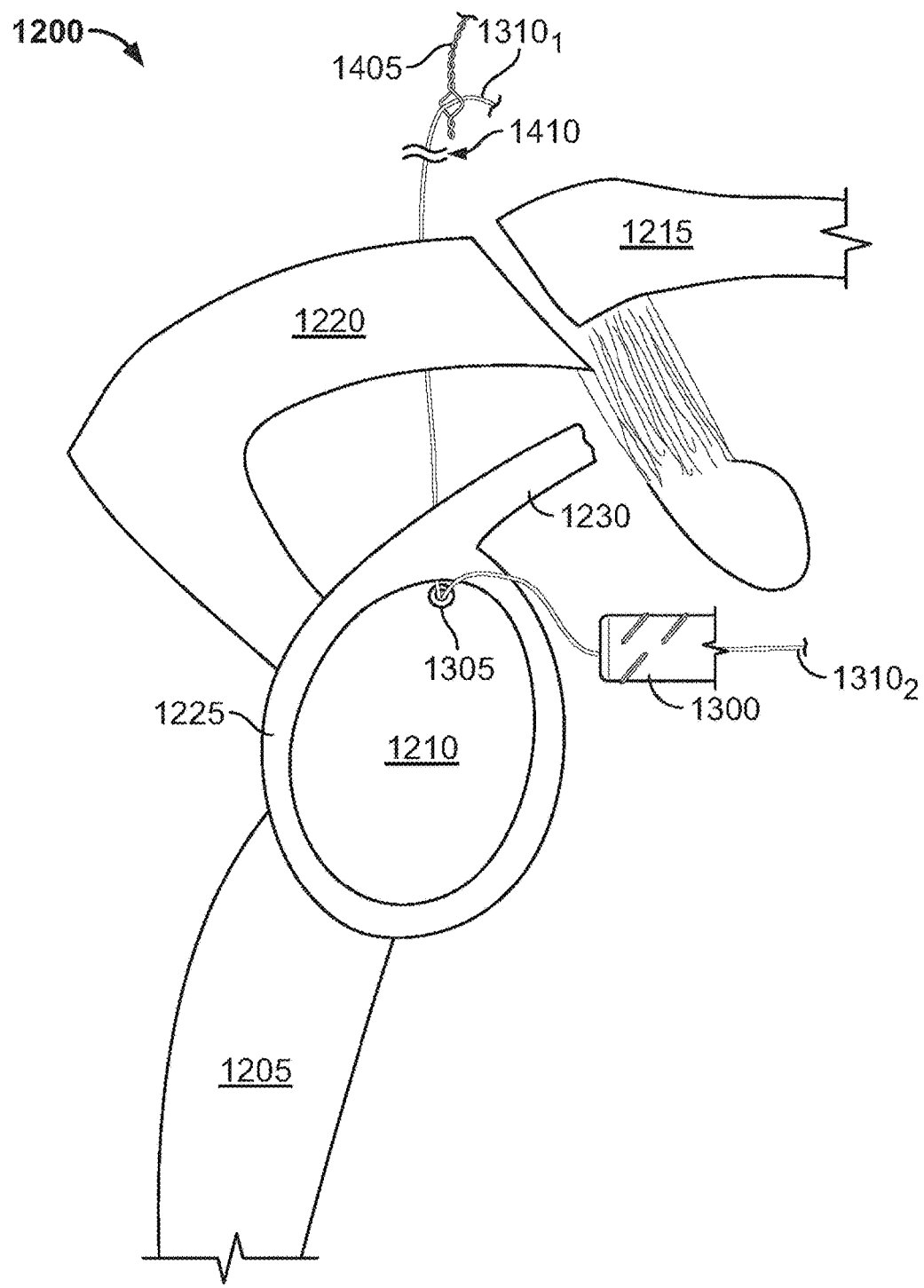

FIG. 17 is a view subsequent to the FIG. 16 view in which the suture transport has retracted one of the suture strands through the portal and through the suture path defined by the percutaneous delivery system. The two suture ends were passed through the loop end (aperture portion 1500) of suture transport 1405 and transport 1405 was removed leaving suture 1310$_1$ exiting through the skin. The suture end closest to labrum 1225 is pulled back through the anterior cannula (portal 1300) using a grasper.

Figure 18:
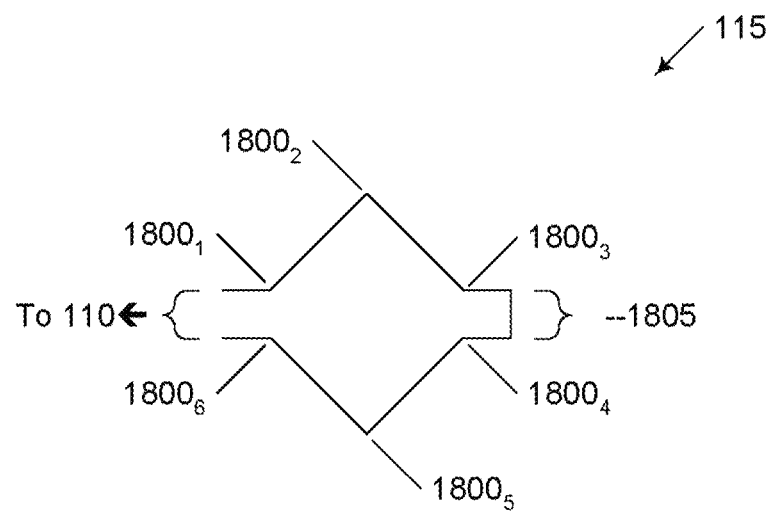
FIG. 18 is a side plan view of a first preferred embodiment for an aperture portion of a suture transport.
Figure 19:
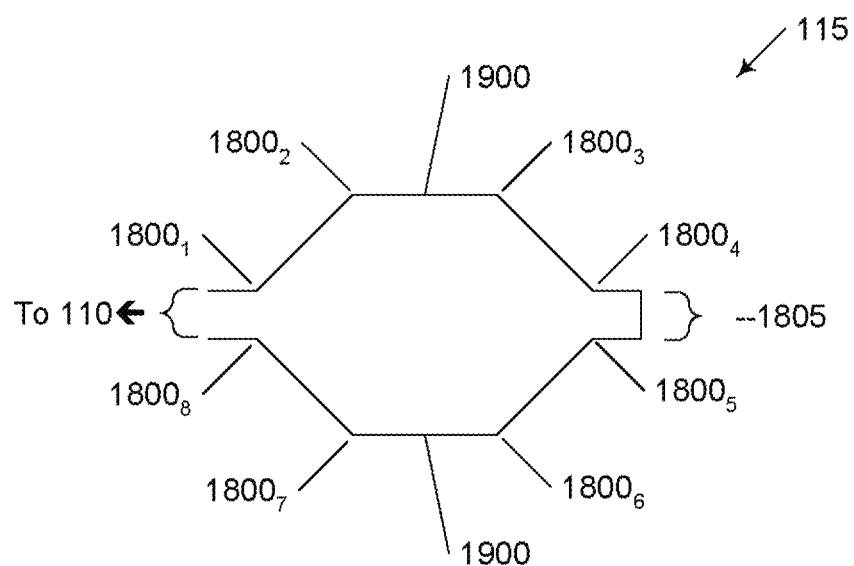
FIG. 19 is a side plan view of a second preferred embodiment for an aperture portion of a suture transport.

FIG. 18 is a side plan view of a first preferred embodiment for aperture portion 115 of a suture transport described herein. Aperture portion 115 is most preferably configured to include a series of hard discrete bends 1800$_i$, i=1 to n that complete a closed loop. When n is equal to 6 (first embodiment FIG. 18) or n is equal to 8 (second embodiment FIG. 19) then a desirable configuration for aperture portion 115 is achieved as further explained below. FIG. 19 is a side plan view of a second preferred embodiment for aperture portion 115 of a suture transport including an aperture extending portion 1900 inserted between each of two pairs of angles of the embodiment shown in FIG. 18 to produce a generalized elongated hexagon shape. In the various embodiments of the present invention, n may vary but is generally an even number that is 6 or greater (6 and 8 being the preferred values), though other configurations are possible.

For simplicity, the optional leader 120 shown, for example, in FIG. 1, is depicted schematically as leader 1805 in FIG. 18 and FIG. 19. The preferred embodiment includes a short twist to end portion 1805 (not shown for clarity) which may be one or more twists in length. In general for many applications it is desirable to have leader 1805 be less than three twists, and most preferably a single twist or a portion of a complete twist. Leader 1805 joins aperture portion 115 at a pair of bends. Body portion 110 (not shown in FIG. 18 and FIG. 19) also joins aperture portion 115 at a second pair of bends.

The configuration of the angles as described by this embodiment with hard angles joined at the twists improves the opening and closing of aperture portion 115 to increase reliability and improve the size of the enclosed area of the loop. It, along with use of non-shearing cross-sectional profiles of the filaments, also enables the expansion and contraction of aperture portion 115 to be implemented by a scissoring action to form a scissor trap.

During some operations, a very large pull force is applied to transport 100 and it is desirable to trap reliably a suture within aperture portion 115. The hard angles, particularly those proximate leader portion 1805, assist in retaining the suture within aperture portion 115 while pulling, particularly while applying relatively large pull forces that may exceed a hundred foot-pounds. Additionally, in some instances, it is possible for an operator to purposely use the scissor trap by passing a suture through aperture portion 115 and then retracting body portion 110 into a channel (e.g., the channel of the percutaneous delivery system) to begin to collapse aperture portion 110 onto the suture using the scissoring action implemented by the bends and their relative configuration to other elements. This scissor trap makes it possible to very securely grip the suture and enabling relatively large pull forces that may equal or exceed 500 foot-pounds of pulling force. Maintaining the engagement of the scissor trap is achieved by the relative location of the transport within the channel. In some instances, leader portion 1805 may have a different configuration to improve trapping for pulling.

In many instances, particularly for configurations supporting large pulling forces (but not exclusively for this purpose), it is preferred that aperture portion 115 be of a single monofilament of shape memory material sized to fit a twisted strand within the channel; in contrast to a twisted braided multi-filament. One potential drawback of braided multi-filament used in aperture portion 115 is that it is very difficult to exactly match lengths properly resulting in uneven load distributions that may cause cascading failures of the individual filaments, thus causing the entire aperture portion 115 to fail.

In some embodiments, it may be desirable to insert an inner moveable sheath or channel into the percutaneous delivery system. In such instances, transport 100 is sized for the inner dimensions of this sheath.

The percutaneous delivery subsystem is a skin-piercing/puncturing system different from systems and methods that make an incision to form all or part of the portal or opening, including those that insert cannulas, and most preferably provide a pair of openings—one exterior to the body and one interior proximate a desired delivery point. These non-piercing/non-puncturing systems are more traumatic to the tissue than insertion of a small gauge (e.g., 18 gauge or smaller diameter). The fine gauge permits precise and simple placement of a suture at virtually any location. When desired, the percutaneous delivery subsystem and transport may be used for multistage suture path definition or discrete definition of suture path segments, at the option of the operator in any specific case. Thus the embodiments are simple and efficient, applicable to many situations and implementations.

In the description herein, numerous specific details are provided, such as examples of components and/or methods, to provide a thorough understanding of embodiments of the present invention. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A percutaneous suture management system for a suture disposed inside a body cavity having a portion of skin overlying the body cavity and configured to be delivered into the body cavity by a tissue-penetrating member including a proximal end and a distal end opposing said proximal end, the distal end having a skin-piercing element configured to pierce the portion of skin with the tissue-penetrating member having an internal channel extending between a proximal opening at the proximal end and a distal opening at the distal end, the distal opening proximate the skin-piercing element and the internal channel having an inner diameter and a channel length, comprising: a discrete member independent from the tissue-penetrating member and configured to be delivered through the internal channel from one of the ends to the other of the ends, said discrete member including a single rigid shape memory alloy monofilament wound about itself and producing both a wound body portion and an aperture portion, said body portion having a body portion width less than the inner diameter and a body portion length greater than the channel length, said aperture portion including an expanded configuration having an expanded width greater than the inner diameter and a collapsed configuration having a collapsed width less than the inner diameter, said aperture portion configured to transition from said expanded configuration to said collapsed configuration when entering into the proximal opening and when entering into the distal opening, and further said aperture portion configured to automatically expand from said collapsed configuration to said expanded configuration when exiting from said proximal opening and when exiting from said distal opening; wherein said aperture portion is configured to form a predetermined perimeter having N number of hard discrete bends, wherein N is an even number that is 6 or greater.

2. The percutaneous suture management system of claim 1 wherein N is equal to 6.

3. The percutaneous suture management system of claim 1 wherein N is equal to 8.

4. The percutaneous suture management system of claim 3 wherein said predetermined perimeter is a generalized elongated hexagon shape.

5. The percutaneous suture management system of claim 1 wherein said single rigid shape memory alloy monofilament further produces a leader portion extending from said aperture portion to an end of said discrete member opposite of said wound body portion, said leader portion configured to join said aperture portion at a pair of said hard discrete bends with said leader portion including a twisted portion of said single rigid shape memory alloy monofilament.

6. The percutaneous suture management system of claim 5 wherein said twisted portion includes at least one complete twist and less than three twists of said single rigid shape memory alloy monofilament.

7. The percutaneous suture management system of claim 5 wherein said leader portion has a leader portion width less than said channel diameter.

8. The percutaneous suture management system of claim 1 wherein said discrete member is configured with said body portion rigid to be pushed/pulled through the internal channel while said aperture portion repeatedly transitions between said expanded mode and said collapsed mode permitting multiple uses of said discrete member.

9. The percutaneous suture management system of claim 1 wherein said discrete member is configured to support a pull force loading of at least a hundred foot-pounds.

10. The percutaneous suture management system of claim 1 wherein said single rigid shape memory monofilament includes a metal shape memory material.

11. The percutaneous suture management system of claim 1 wherein the tissue-penetrating member includes a needle having a needle gauge no larger than an 18 gauge.

12. The percutaneous suture management system of claim 1 wherein said skin-piercing element includes a needle having a nominal outside diameter no larger than an 18 needle gauge.

13. The percutaneous suture management system of claim 11 wherein said needle includes an axial longitudinal channel that includes said internal channel.

14. The percutaneous suture management system of claim 1 wherein the channel diameter is no greater than an 18 needle gauge nominal inner diameter.

15. The percutaneous suture management system of claim 14 wherein N is equal to 6.

16. The percutaneous suture management system of claim 14 wherein N is equal to 8.

17. The percutaneous suture management system of claim 16 wherein said predetermined perimeter is a generalized elongated hexagon shape.

18. The percutaneous suture management system of claim 14 wherein said single rigid shape memory alloy monofilament further produces a leader portion extending from said aperture portion to an end of said discrete member opposite of said wound body portion, said leader portion configured to join said aperture portion at a pair of said hard discrete bends with said leader portion including a twisted portion of said single rigid shape memory alloy monofilament.

19. The percutaneous suture management system of claim 18 wherein said twisted portion includes at least one complete twist and less than three twists of said single rigid shape memory alloy monofilament.

20. The percutaneous suture management system of claim 18 wherein said leader portion has a leader portion width less than said channel diameter.

21. The percutaneous suture management system of claim 14 wherein said discrete member is configured with said body portion rigid to be pushed/pulled through the internal channel while said aperture portion repeatedly transitions between said expanded mode and said collapsed mode permitting multiple uses of said discrete member.

22. The percutaneous suture management system of claim 14 wherein said discrete member is configured to support a pull force loading of at least a hundred foot-pounds.

23. The percutaneous suture management system of claim 14 wherein said single rigid shape memory monofilament includes a metal shape memory material.

24. The percutaneous suture management system of claim 14 wherein the tissue-penetrating member includes a needle having a needle gauge no larger than an 18 gauge.

25. The percutaneous suture management system of claim 14 wherein said skin-piercing element includes a needle having a nominal outside diameter no larger than an 18 needle gauge.

26. The percutaneous suture management system of claim 24 wherein said needle includes an axial longitudinal channel that includes said internal channel.

27. The percutaneous suture management system of claim 1 wherein said discrete member consists essentially of said single rigid shape memory alloy monofilament wound about itself.

28. A suture management apparatus for cooperation with a delivery system defining an internal channel extending between a first end and a second end spaced apart from said first end by a channel length, the internal channel having an inner diameter, comprising:

a discrete member independent from the delivery system and configured to be delivered through the internal channel from one of the ends to the other of the ends, said discrete member including a single rigid shape memory alloy monofilament wound about itself and producing both a wound body portion and an aperture portion, said body portion having a body portion width less than the inner diameter and a body portion length greater than the channel length, said aperture portion including an expanded configuration having an expanded width greater than the inner diameter and a collapsed configuration having a collapsed width less than the inner diameter, said aperture portion configured to transition from said expanded configuration to said collapsed configuration when entering into either of the ends, and further said aperture portion configured to automatically expand from said collapsed configuration to said expanded configuration when exiting from either of the ends; wherein said aperture portion is configured to form a predetermined perimeter having N number of hard discrete bends, wherein N is a number that is 6 or greater.

29. The suture management apparatus of claim 28 wherein N is equal to 6.

30. The suture management apparatus of claim 28 wherein N is equal to 8.

31. The suture management apparatus of claim 30 wherein said predetermined perimeter is a generalized elongated hexagon shape.

32. The suture management apparatus of claim 28 wherein said single rigid shape memory alloy monofilament further produces a leader portion extending from said aperture portion to an end of said discrete member opposite of said wound body portion, said leader portion configured to join said aperture portion at a pair of said hard discrete bends with said leader portion including a twisted portion of said single rigid shape memory alloy monofilament.

33. The suture management apparatus of claim 32 wherein said twisted portion includes at least one complete twist and less than three twists of said single rigid shape memory alloy monofilament.

34. The suture management apparatus of claim 32 wherein said leader portion has a leader portion width less than the channel diameter.

35. The suture management apparatus of claim 28 wherein said discrete member is configured with said body portion rigid to be pushed/pulled through the internal channel while said aperture portion repeatedly transitions between said expanded mode and said collapsed mode permitting multiple uses of said discrete member.

36. The suture management apparatus of claim 28 wherein said discrete member is configured to support a pull force loading of at least a hundred foot-pounds.

37. The suture management apparatus of claim 28 wherein said single rigid shape memory monofilament includes a metal shape memory material.

38. The suture management apparatus of claim 28 wherein the delivery system includes a needle having a needle gauge no larger than an 18 gauge.

39. The suture management apparatus of claim 38 wherein said needle includes an axial longitudinal channel that includes the internal channel.

40. The suture management apparatus of claim 28 wherein delivery system includes a needle having a nominal outside diameter no larger than an 18 needle gauge.

41. The suture control apparatus of claim 28 wherein said discrete member is further configured to be inserted into both ends of the internal channel.

42. The suture control apparatus of claim 28 wherein said discrete member consists essentially of said single rigid shape memory alloy monofilament wound about itself.

43. A suture control apparatus for cooperation with a percutaneous delivery system defining an internal channel extending between a first end and a second end spaced apart from said first end by a channel length, the internal channel having an inner diameter, comprising:

a discrete member independent from the percutaneous delivery system and configured to be delivered through the internal channel from one of the ends to the other of the ends, said discrete member including a single rigid shape memory alloy monofilament wound about itself and producing both a wound body portion and an aperture portion, said body portion having a body portion width less than the inner diameter and a body portion length greater than the channel length, said aperture portion including an expanded configuration having an expanded width greater than the inner diameter and a collapsed configuration having a collapsed width less than the inner diameter, said aperture portion configured to transition from said expanded configuration to said collapsed configuration when entering into either of the ends, and further said aperture portion configured to automatically expand from said collapsed configuration to said expanded configuration when exiting from either of the ends; wherein said aperture portion is configured to form a predetermined perimeter having N number of hard discrete bends, wherein N is a number that is 6 or greater.

44. The suture control apparatus of claim 43 wherein said discrete member is further configured to be inserted into both ends of the internal channel.

45. The suture control apparatus of claim 43 wherein said discrete member consists essentially of said single rigid shape memory alloy monofilament wound about itself.

* * * * *